United States Patent
Carpenter et al.

(10) Patent No.: US 8,805,526 B2
(45) Date of Patent: Aug. 12, 2014

(54) CONFIGURABLE MEDICAL TELEMETRY RADIO SYSTEM

(75) Inventors: Greg Carpenter, Centerville, MN (US); Joseph E. Bánge, Egan, MN (US); Peter J. Musto, Prior Lake, MN (US); William R. Mass, Maple Grove, MN (US); Jonathan Hedstrom, Grand Marais, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 823 days.

(21) Appl. No.: 11/381,493

(22) Filed: May 3, 2006

(65) Prior Publication Data

US 2007/0260293 A1  Nov. 8, 2007

(51) Int. Cl.
*A61N 1/00* (2006.01)
*A61N 1/372* (2006.01)

(52) U.S. Cl.
CPC .................................. *A61N 1/3727* (2013.01)
USPC .......................................................... 607/60

(58) Field of Classification Search
CPC ........... A61N 1/37217; A61N 1/37247; A61N 1/37252; A61N 1/37235; A61B 5/0002; A61B 5/0004; A61B 5/0015; A61B 5/0031
USPC ........................ 607/32, 60, 156; 128/903, 904
See application file for complete search history.

(56) References Cited

U.S. PATENT DOCUMENTS

| | | | |
|---|---|---|---|
| 4,341,982 A | 7/1982 | Lahti et al. | |
| 4,404,972 A | 9/1983 | Gordon et al. | |
| 4,441,498 A | 4/1984 | Nordling | |
| 4,542,535 A | 9/1985 | Bates et al. | |
| 4,543,954 A | 10/1985 | Cook et al. | |
| 4,561,443 A | 12/1985 | Hogrefe et al. | |
| 4,562,841 A | 1/1986 | Brockway et al. | |
| 4,731,814 A | 3/1988 | Becker et al. | |
| 4,944,299 A | 7/1990 | Silvian | |
| 4,945,909 A | 8/1990 | Fearnot et al. | |
| 4,987,897 A | 1/1991 | Funke | |
| 5,025,808 A | 6/1991 | Hafner | |

(Continued)

FOREIGN PATENT DOCUMENTS

| | | |
|---|---|---|
| EP | 0607638 A2 | 7/1994 |
| WO | WO-03/053515 A1 | 7/2003 |
| WO | WO-2006/020546 A1 | 2/2006 |
| WO | WO-2006/020549 A1 | 2/2006 |

OTHER PUBLICATIONS

Guidant, "Feature Sheet and Specifications: Zoom Latitude", Doc. No. C3-194-1005 (2005),2 pgs.

(Continued)

*Primary Examiner* — Christopher D Koharski
*Assistant Examiner* — Roland Dinga
(74) *Attorney, Agent, or Firm* — Schwegman, Lundberg & Woessner, P.A.

(57) ABSTRACT

A system including an external medical data telemetry device to communicate with an implantable medical device (IMD). The external medical data telemetry device includes a processor, a reconfigurable radio-frequency (RF) transceiver circuit, at least one far-field antenna, and a user interface. The reconfigurable RF transceiver circuit modulates an outgoing IMD data signal and demodulates an incoming IMD data signal using a modulation type that is selectable from a plurality of modulation types by the processor. The processor selects the modulation type using information entered by a user through the user interface.

20 Claims, 13 Drawing Sheets

(56) References Cited

U.S. PATENT DOCUMENTS

| | | | |
|---|---|---|---|
| 5,107,833 A | 4/1992 | Barsness | |
| 5,113,869 A | 5/1992 | Nappholz et al. | |
| 5,292,343 A | 3/1994 | Blanchette et al. | |
| 5,314,453 A | 5/1994 | Jeutter | |
| 5,342,408 A * | 8/1994 | deCoriolis et al. | 607/32 |
| 5,350,412 A | 9/1994 | Hoegnelid et al. | |
| 5,370,666 A | 12/1994 | Lindberg et al. | |
| 5,404,877 A | 4/1995 | Nolan et al. | |
| 5,466,246 A * | 11/1995 | Silvian | 607/32 |
| 5,476,488 A | 12/1995 | Morgan et al. | |
| 5,532,708 A | 7/1996 | Krenz et al. | |
| 5,577,087 A * | 11/1996 | Furuya | 375/377 |
| 5,579,876 A | 12/1996 | Adrian et al. | |
| 5,593,430 A | 1/1997 | Renger | |
| 5,603,331 A * | 2/1997 | Heemels et al. | 600/508 |
| 5,650,759 A | 7/1997 | Hittman et al. | |
| 5,683,432 A | 11/1997 | Goedeke et al. | |
| 5,694,952 A | 12/1997 | Lidman et al. | |
| 5,697,958 A | 12/1997 | Paul et al. | |
| 5,733,313 A * | 3/1998 | Barreras et al. | 607/33 |
| 5,752,976 A | 5/1998 | Duffin et al. | |
| 5,752,977 A | 5/1998 | Grevious et al. | |
| 5,759,199 A * | 6/1998 | Snell et al. | 607/60 |
| 5,764,699 A * | 6/1998 | Needham et al. | 375/261 |
| 5,766,232 A | 6/1998 | Grevious et al. | |
| 5,807,397 A * | 9/1998 | Barreras | 607/61 |
| 5,843,139 A * | 12/1998 | Goedeke et al. | 607/32 |
| 5,861,019 A | 1/1999 | Sun et al. | |
| 6,009,350 A | 12/1999 | Renken | |
| 6,083,248 A | 7/2000 | Thompson | |
| 6,093,146 A | 7/2000 | Filangeri | |
| 6,115,583 A | 9/2000 | Brummer et al. | |
| 6,115,634 A | 9/2000 | Donders et al. | |
| 6,115,636 A | 9/2000 | Ryan | |
| 6,128,528 A | 10/2000 | Erickson et al. | |
| 6,155,208 A | 12/2000 | Schell et al. | |
| 6,167,312 A | 12/2000 | Goedeke | |
| 6,169,925 B1 | 1/2001 | Villaseca et al. | |
| 6,200,265 B1 | 3/2001 | Walsh et al. | |
| 6,223,083 B1 | 4/2001 | Rosar | |
| 6,240,317 B1 | 5/2001 | Villaseca et al. | |
| 6,263,246 B1 | 7/2001 | Goedeke et al. | |
| 6,275,737 B1 | 8/2001 | Mann | |
| 6,329,920 B1 | 12/2001 | Morrison et al. | |
| 6,336,903 B1 | 1/2002 | Bardy | |
| 6,388,628 B1 | 5/2002 | Dettloff et al. | |
| 6,400,990 B1 | 6/2002 | Silvian | |
| 6,424,867 B1 | 7/2002 | Snell et al. | |
| 6,427,088 B1 | 7/2002 | Bowman, IV et al. | |
| 6,434,429 B1 | 8/2002 | Kraus et al. | |
| 6,443,891 B1 * | 9/2002 | Grevious | 600/302 |
| 6,453,198 B1 | 9/2002 | Torgerson et al. | |
| 6,456,256 B1 | 9/2002 | Amundson et al. | |
| 6,470,215 B1 | 10/2002 | Kraus et al. | |
| 6,482,154 B1 | 11/2002 | Haubrich et al. | |
| 6,490,487 B1 | 12/2002 | Kraus et al. | |
| 6,505,072 B1 | 1/2003 | Linder et al. | |
| 6,527,729 B1 | 3/2003 | Turcott | |
| 6,531,982 B1 | 3/2003 | White et al. | |
| 6,535,766 B1 | 3/2003 | Thompson et al. | |
| 6,562,000 B2 | 5/2003 | Thompson et al. | |
| 6,564,104 B2 | 5/2003 | Nelson et al. | |
| 6,564,105 B2 | 5/2003 | Starkweather et al. | |
| 6,574,509 B1 | 6/2003 | Kraus et al. | |
| 6,574,510 B2 | 6/2003 | Von Arx et al. | |
| 6,577,900 B1 | 6/2003 | Silvian | |
| 6,577,901 B2 | 6/2003 | Thompson et al. | |
| 6,585,644 B2 | 7/2003 | Lebel et al. | |
| 6,600,952 B1 | 7/2003 | Snell et al. | |
| 6,609,029 B1 | 8/2003 | Mann et al. | |
| 6,614,406 B2 | 9/2003 | Amundson et al. | |
| 6,622,043 B1 | 9/2003 | Kraus et al. | |
| 6,622,050 B2 | 9/2003 | Thompson | |
| 6,624,786 B2 | 9/2003 | Boyle | |
| 6,648,821 B2 | 11/2003 | Lebel et al. | |
| 6,659,948 B2 | 12/2003 | Lebel et al. | |
| 6,671,328 B1 * | 12/2003 | Poon et al. | 375/295 |
| 6,675,045 B2 | 1/2004 | Mass et al. | |
| 6,687,546 B2 | 2/2004 | Lebel et al. | |
| 6,708,065 B2 | 3/2004 | Von Arx et al. | |
| 6,716,165 B1 | 4/2004 | Flanders et al. | |
| 6,741,886 B2 | 5/2004 | Yonce | |
| 6,804,559 B1 | 10/2004 | Kraus et al. | |
| 6,809,701 B2 | 10/2004 | Amundson et al. | |
| 6,844,854 B2 | 1/2005 | Johnson et al. | |
| 6,889,081 B2 | 5/2005 | Hsu | |
| 6,985,088 B2 | 1/2006 | Goetz et al. | |
| 6,985,773 B2 | 1/2006 | Von Arx et al. | |
| 6,993,393 B2 | 1/2006 | Von Arx et al. | |
| 7,047,076 B1 | 5/2006 | Li et al. | |
| 7,069,086 B2 | 6/2006 | Von Arx | |
| 7,107,085 B2 | 9/2006 | Doi | |
| 7,110,823 B2 | 9/2006 | Whitehurst et al. | |
| 7,228,182 B2 | 6/2007 | Healy et al. | |
| 7,319,903 B2 | 1/2008 | Bange et al. | |
| 7,359,753 B2 | 4/2008 | Bange et al. | |
| 7,610,065 B2 | 10/2009 | Vallapureddy et al. | |
| 7,668,596 B2 | 2/2010 | Von Arx et al. | |
| 7,729,776 B2 | 6/2010 | Von Arx et al. | |
| 7,738,964 B2 | 6/2010 | Von Arx et al. | |
| 7,818,067 B2 | 10/2010 | Healy et al. | |
| 7,860,574 B2 | 12/2010 | Von Arx et al. | |
| 8,041,432 B2 | 10/2011 | Von Arx et al. | |
| 8,046,080 B2 | 10/2011 | Von Arx et al. | |
| 8,238,975 B2 | 8/2012 | Vallapureddy et al. | |
| 8,538,528 B2 | 9/2013 | Von Arx et al. | |
| 2001/0001014 A1 | 5/2001 | Akins et al. | |
| 2001/0027331 A1 | 10/2001 | Thompson | |
| 2001/0047125 A1 | 11/2001 | Quy | |
| 2002/0013614 A1 | 1/2002 | Thompson | |
| 2002/0019606 A1 | 2/2002 | Lebel et al. | |
| 2002/0049480 A1 | 4/2002 | Lebel et al. | |
| 2002/0065539 A1 | 5/2002 | Von Arx et al. | |
| 2002/0065540 A1 | 5/2002 | Lebel et al. | |
| 2002/0147388 A1 * | 10/2002 | Mass et al. | 600/300 |
| 2002/0159545 A1 * | 10/2002 | Ramesh et al. | 375/340 |
| 2003/0018369 A1 | 1/2003 | Thompson et al. | |
| 2003/0028902 A1 | 2/2003 | Cubley et al. | |
| 2003/0041866 A1 * | 3/2003 | Linberg et al. | 128/899 |
| 2003/0083719 A1 | 5/2003 | Shankar et al. | |
| 2003/0114897 A1 | 6/2003 | Von Arx et al. | |
| 2003/0114898 A1 * | 6/2003 | Von Arx et al. | 607/60 |
| 2003/0135246 A1 * | 7/2003 | Mass et al. | 607/60 |
| 2003/0149459 A1 | 8/2003 | Von Arx et al. | |
| 2003/0174069 A1 | 9/2003 | Goetz et al. | |
| 2003/0216793 A1 | 11/2003 | Karlsson et al. | |
| 2004/0030260 A1 | 2/2004 | Von Arx | |
| 2004/0102815 A1 | 5/2004 | Balczewski et al. | |
| 2004/0106967 A1 * | 6/2004 | Von Arx et al. | 607/60 |
| 2004/0167587 A1 * | 8/2004 | Thompson | 607/60 |
| 2004/0247047 A1 * | 12/2004 | Dennis et al. | 375/320 |
| 2004/0260363 A1 | 12/2004 | Arx et al. | |
| 2004/0263273 A1 * | 12/2004 | Ahmed | 332/103 |
| 2005/0204134 A1 | 9/2005 | Von Arx et al. | |
| 2005/0240245 A1 * | 10/2005 | Bange et al. | 607/60 |
| 2005/0261934 A1 | 11/2005 | Thompson | |
| 2005/0283208 A1 | 12/2005 | Von Arx et al. | |
| 2005/0288738 A1 | 12/2005 | Bange et al. | |
| 2006/0025834 A1 | 2/2006 | Von Arx et al. | |
| 2006/0030901 A1 | 2/2006 | Quiles et al. | |
| 2006/0030902 A1 | 2/2006 | Quiles et al. | |
| 2006/0030903 A1 | 2/2006 | Seeberger et al. | |
| 2006/0111054 A1 | 5/2006 | Pan et al. | |
| 2006/0116744 A1 | 6/2006 | Von Arx et al. | |
| 2006/0194615 A1 | 8/2006 | Vallapureddy et al. | |
| 2010/0045480 A1 | 2/2010 | Vallapureddy et al. | |
| 2010/0106224 A1 | 4/2010 | Von Arx et al. | |
| 2010/0114233 A1 | 5/2010 | Von Arx et al. | |
| 2010/0152816 A1 | 6/2010 | Von Arx et al. | |
| 2011/0066211 A1 | 3/2011 | Von Arx et al. | |
| 2014/0012341 A1 | 1/2014 | Von Arx et al. | |

OTHER PUBLICATIONS

Guidant, "Go Beyond the Wand", Doc. No. C3-107-0505, (2005),2 pgs.

(56) References Cited

OTHER PUBLICATIONS

Guidant, "Think Beyond the Wand", Doc. No. C3-101-0505, (2005),3 pgs.
Guidant, "What if you could ZIP through implants and follow ups?", Doc. No. C3-117-0505, (2005),2 pgs.
Guidant, "What if your patient develops diaphragmatic stimulation?", Doc. No. C3-116-0505, (2005),2 pgs.
Harney, Austin, et al., "Wireless Short-Range Devices: Designing a Global License-Free System for Frequencies <1 GHz", *Analog Dialogue* 40-03, (Mar. 2006),1 pg.
Zarlink Semiconductor, "Medical Implantable RF Transceiver", (2005),40 pgs.
"U.S. Appl. No. 11/068,478, Response filed Aug. 4, 2008 to Final Office Action mailed Jun. 2, 2008", 19 pgs.
"U.S. Appl. No. 11/325,584, Response filed Jul. 10, 2008 to Non Final Office Action mailed Apr. 10, 2008", 9 pgs.
"U.S. Appl. No. 10/025,183 Notice of Allowance Mailed Sep. 14, 2007", 4 pgs.
"U.S. Appl. No. 10/025,183 Response filed May 12, 2008 to Non-Final Office Action mailed Dec. 10, 2007", 10 pgs.
"U.S. Appl. No. 10/025,183 Non-Final Office Action mailed Feb. 15, 2006", 5 pgs.
"U.S. Appl. No. 10/025,183 Non-Final Office Action mailed Dec. 10, 2007", 4 Pgs.
"U.S. Appl. No. 10/025,183 Amendment and Response filed Jan. 31, 2007 to Final Office Action mailed Jul. 31, 2006", 11 pgs.
"U.S. Appl. No. 10/025,183 Amendment and Response filed Apr. 13, 2005 to Final Office Action mailed Jan. 13, 2005", 11 pgs.
"U.S. Appl. No. 10/025,183 Amendment and Response filed Jun. 2, 2004 to Non-Final Office Action mailed 3-4-1004", 11 pgs.
"U.S. Appl. No. 10/025,183 Amendment and Response filed Jun. 26, 2007 to Non-Final Office Action mailed Mar. 26, 2007", 14 pgs.
"U.S. Appl. No. 10/025,183 Appeal Brief filed Jan. 3, 2006", 27 pgs.
"U.S. Appl. No. 10/025,183 Final Office Action mailed Jan. 13, 2005", 7 pgs.
"U.S. Appl. No. 10/025,183 Final Office Action mailed May 25, 2005", 9 pgs.
"U.S. Appl. No. 10/025,183 Final Office Action mailed Jul. 31, 2006", 7 pgs.
"U.S. Appl. No. 10/025,183 Final Office Action mailed Aug. 3, 2004", 7 pgs.
"U.S. Appl. No. 10/025,183 Non-Final Office Action Mar. 4, 2004", 5 pgs.
"U.S. Appl. No. 10/025,183 Non-Final Office Action mailed Mar. 26, 2007", 4 pgs.
"U.S. Appl. No. 10/025,183 Response filed Dec. 3, 2004 to Final Office Action mailed Aug. 3, 2004", 11 pgs.
"U.S. Appl. No. 10/025,183 Response filed May 15, 2006 to Non-Final Office Action mailed Feb. 15, 2006", 11 pgs.
"U.S. Appl. No. 10/025,223 Final Office Action mailed Aug. 16, 2004", 8 pgs.
"U.S. Appl. No. 10/025,223 Final Office Action mailed Sep. 10, 2004", 7 pgs.
"U.S. Appl. No. 10/025,223 Non-Final Office Action mailed Mar. 1, 2005", 6 pgs.
"U.S. Appl. No. 10/025,223 Non-Final Office Action mailed Mar. 19, 2004", 5 pgs.
"U.S. Appl. No. 10/025,223 Final Office Action mailed Aug. 16, 2004", 9 pgs.
"U.S. Appl. No. 10/025,223 Non Final Office Action mailed Mar. 1, 2005", 8 pgs.
"U.S. Appl. No. 10/025,223 Non Final Office Action mailed Mar. 19, 2004", 6 pgs.
"U.S. Appl. No. 10/071,255 Non Final Office Action mailed Jan. 7, 2005", 6 pgs.
"U.S. Appl. No. 10/071,255 Response filed Apr. 7, 2005 to Non-Final Office Action mailed Jan. 7, 2005", 12 pgs.
"U.S. Appl. No. 10/252,494 Non Final Office Action mailed Jan. 30, 2003", 6 pgs.
"U.S. Appl. No. 10/269,905 Non Final Office Action mailed Jul. 27, 2005", 15 pgs.
"U.S. Appl. No. 10/744,943 Final Office Action mailed Feb. 21, 2008", 15 pgs.
"U.S. Appl. No. 10/914,496 Non-Final Office Action mailed Mar. 18, 2008", 9 pgs.
"U.S. Appl. No. 10/914,496 Final office action mailed May 23, 2007", 11 pgs.
"U.S. Appl. No. 10/914,496 Non Final office action mailed Dec. 5, 2006", 12 pgs.
"U.S. Appl. No. 10/914,499 Final Office Action mailed Jan. 24, 2008", 10 pgs.
"U.S. Appl. No. 10/914,499 Non-Final Office Action mailed May 29, 2007", 14 pgs.
"U.S. Appl. No. 10/914,638 Final Office Action mailed Apr. 17, 2007", 10 pgs.
"U.S. Appl. No. 10/914,638 Non-Final Office Action mailed Oct. 18, 2006", 13 pgs.
"U.S. Appl. No. 11/068,478, Response filed Mar. 17, 2008 to Non-Final Office Action mailed Dec. 17, 2007", 19 pgs.
"U.S. Appl. No. 11/068,478 Non-Final Office Action mailed Dec. 17, 2007", 15 pgs.
"U.S. Appl. No. 11/068,478 Final Office Action mailed Jun. 2, 2008", 17 pgs.
"U.S. Appl. No. 11/101,142 Non-Final Office Action mailed Jun. 20, 2007", 8 pgs.
"U.S. Appl. No. 11/101,196 Non Final Office Action mailed Mar. 29, 2007", 8 pgs.
"U.S. Appl. No. 11/325,584 Non-Final Office Action mailed Apr. 10, 2008", 6 pgs.
"International Application No. PCT/US02/40488, International Search Report mailed May 9, 2003", 7 pgs.
"International Application No. PCT/US03/03748, International Search Report mailed Oct. 20, 2003", 5 pgs.
"International Application No. PCT/US2005/028052 International Preliminary Report on Patentability mailed Feb. 22, 2007", 8 pgs.
"International Application No. PCT/US2005/028052 International Search Report and Written Opinion mailed Nov. 29, 2005", 12 pgs.
"International Application No. PCT/US2005/028059 International Preliminary Report on Patentability mailed Feb. 13, 2007", 9 pgs.
"International Application No. PCT/US2005/028059 International Search Report and Written Opinion mailed Jan. 12, 2005", 13 pgs.
"Prosecution File History for U.S. Appl. No. 10/025,223", 55 pgs.
"Prosecution File History for U.S. Appl. No. 10/914,496", 56 pgs.
"Prosecution File History of U.S. Appl. No. 10/269,905, filed Oct. 11, 2002, Prosecution File History", (now US 7,069,086),32 pgs.
Bange, J. E., et al., "System and Method for RF Transceiver Duty Cycling in an Implantable Medical Device", U.S. Appl. No. 11/101,196, filed Apr. 7, 2005, 19 pgs.
Quiles, S., "Automatic Power Control for a Radio Frequency Transceiver of an Implantable Device", U.S. Appl. No. 10/914,496, filed Aug. 9, 2004, 23 pgs.
Quiles, S., "Telemetry Switchover State Machine With Firmware Priority Control", U.S. Appl. No. 10/914,499, filed Aug. 9, 2004, 30 pgs.
Rawat, P., et al., "Radio Frequency Antenna in a Header of an Implantable Medical Device", U.S. Appl. No. 10/744,943, filed Dec. 22, 2003, 34 pgs.
Seeberger, M., "Dynamic Telemetry Link Selection for an Implantable Device", U.S. Appl. No. 10/914,638, filed Aug. 9, 2004, 35 pgs.
"U.S. Appl. No. 11/640,552, Examiner Interview Summary mailed Aug. 10 2009", 3 pgs.
"U.S. Appl. No. 12/604,254, Response filed Feb. 29, 2012 to Non Final Office Action mailed Nov. 2, 2011", 9 pgs.
"U.S. Appl. No. 10/025,183, Notice of Allowance mailed Sep. 28, 2009", 5 pgs.
"U.S. Appl. No. 11/068,478, Corrected Notice of Allowance mailed Jun. 19, 2009", 4 pgs.
"U.S. Appl. No. 11/068,478, Non Final Office Action mailed Jan. 2, 2009", 11 pgs.
"U.S. Appl. No. 11/068,478, Notice of Allowance mailed Jun. 9, 2009", 7 pgs.

(56) References Cited

OTHER PUBLICATIONS

"U.S. Appl. No. 11/068,478, Response filed Mar. 30, 2009 to Non Final Office Action mailed Jan. 2, 2009", 20 pgs.
"U.S. Appl. No. 11/068,478, Response filed Nov. 3, 2008 to Advisory Action mailed Sep. 16, 2008", 17 pgs.
"U.S. Appl. No. 11/244,273, Notice of Allowance mailed Oct. 5, 2009", 7 pgs.
"U.S. Appl. No. 11/325,584, Notice of Allowance mailed Mar. 23, 2010", 4 pgs.
"U.S. Appl. No. 11/325,584, Notice of Allowance mailed Oct. 21, 2009", 5 pgs.
"U.S. Appl. No. 11/640,552, Examiner Interview Summary mailed May 27, 2010", 4 pgs.
"U.S. Appl. No. 11/640,552, Examiner Interview Summary mailed Aug. 10, 2009", 3 pgs.
"U.S. Appl. No. 11/640,552, Final Office Action mailed Mar. 24, 2010", 8 pgs.
"U.S. Appl. No. 11/640,552, Non Final Office Action mailed Jul. 29, 2013", 6 pgs.
"U.S. Appl. No. 11/640,552, Notice of Allowance mailed Nov. 25, 2013", 7 pgs.
"U.S. Appl. No. 11/640,552, Response filed Jun. 24, 2010 to Final Office Action mailed Mar. 24, 2010", 9 pgs.
"U.S. Appl. No. 11/640,552, Response filed Oct. 17, 2013 to Non Final Office Action mailed Jul. 29, 2013", 8 pgs.
"U.S. Appl. No. 11/738,942, Non Final Office Action mailed Jan. 20, 2010", 8 pgs.
"U.S. Appl. No. 11/738,942, Notice of Allowance mailed Jun. 17, 2010", 8 pgs.
"U.S. Appl. No. 11/738,942, Response filed Apr. 20, 2010 to Non Final Office Action mailed Jan. 20, 2010", 10 pgs.
"U.S. Appl. No. 11/738,942, Response filed Sep. 16, 2009 to Non Final Office Action mailed Jun. 9, 2009", 9 pgs.
"U.S. Appl. No. 12/604,254, Non Final Office Action mailed Nov. 2, 2011", 7 pgs.
"U.S. Appl. No. 12/604,254, Notice of Allowance mailed Mar. 30, 2012", 5 pgs.
"U.S. Appl. No. 12/604,254, Response filed Feb. 29, 2012 to Non Final Office Action mailed Nov. 2, 2011", 9 pgs.
"U.S. Appl. No. 12/604,254, Supplemental Notice of Allowability mailed Jul. 12, 2012", 2 pgs.
"U.S. Appl. No. 12/648,687, Notice of Allowance mailed Aug. 17, 2010", 7 pgs.
"U.S. Appl. No. 12/684,303, Final Office Action mailed Mar. 4, 2013", 8 pgs.
"U.S. Appl. No. 12/684,303, Non Final Office Action mailed Apr. 5, 2011", 5 pgs.
"U.S. Appl. No. 12/684,303, Non Final Office Action mailed May 2, 2012", 6 pgs.
"U.S. Appl. No. 12/684,303, Notice of Allowance mailed May 24, 2013", 9 pgs.
"U.S. Appl. No. 12/684,303, Response filed Apr. 1, 2013 to Final Office Action mailed Mar. 4, 2013", 9 pgs.
"U.S. Appl. No. 12/684,303, Response filed Jun. 13, 2011 to Non-Final Office Action mailed Apr. 5, 2011", 10 pgs.
"U.S. Appl. No. 12/684,303, Response filed Sep. 6, 2012 to Non Final Office Action mailed May 2, 2012", 8 pgs.
"U.S. Appl. No. 12/713,669, Non-Final Office Action mailed Mar. 2, 2011", 5 pgs.
"U.S. Appl. No. 12/713,669, Notice of Allowance mailed Jun. 24, 2011", 5 pgs.
"U.S. Appl. No. 12/713,669, Response filed May 16, 2011 to Non-Final Office Action mailed Mar. 2, 2011", 8 pgs.
"U.S. Appl. No. 12/950,359, Notice of Allowance mailed Jun. 23, 2011", 7 pgs.
"U.S. Appl. No. 14/019,830, Non Final Office Action mailed Dec. 10, 2013", 8 pgs.
"U.S. Appl. No. 14/019,830, Response filed Feb. 6, 2014 to Non Final Office Action mailed Dec. 10, 2013", 7 pgs.

* cited by examiner

ASK:

FSK:

PSK:

CONFIGURABLE MEDICAL TELEMETRY RADIO SYSTEM

CROSS REFERENCE TO RELATED APPLICATIONS

This application is related to the following co-pending, commonly assigned U.S. patent application Ser. No. 11/068,478 entitled, "METHOD AND APPARATUS FOR ANTENNA SELECTION IN A DIVERSITY ANTENNA SYSTEM FOR COMMUNICATING WITH IMPLANTABLE MEDICAL DEVICE," filed on Feb. 28, 2005, which is hereby incorporated by reference.

TECHNICAL FIELD

The field generally relates to implantable medical devices and, in particular, but not by way of limitation, to systems and methods for communicating with implantable medical devices.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable sensors, implantable insulin pumps, devices implanted to administer drugs to a patient, or implantable devices with neural stimulation capability.

Typically, IMDs communicate wirelessly with an external device. Examples include an IMD programmer that provides bi-directional communication between the IMD and a caregiver, a patient activator that allows a patient to activate an implantable device, a patient data display that reads and displays information from the IMD, and a repeater that communicates with a network and locally communicates information with the IMD. The communication typically follows a protocol of information transfer defined by the IMD type. To communicate with more than one type of IMD, a physician may need more than one type of external programmer or other external device.

SUMMARY

This document discusses, among other things, systems and methods for communicating with implantable medical devices. A system example includes an external medical data telemetry device to communicate with an implantable medical device (IMD). The external medical data telemetry device includes a processor, a reconfigurable radio-frequency (RF) transceiver circuit, at least one far-field antenna, and a user interface. The reconfigurable RF transceiver circuit modulates an outgoing IMD data signal and demodulates an incoming IMD data signal using a modulation type that is selectable from a plurality of modulation types by the processor. The processor selects the modulation type using information entered by a user through the user interface.

A method example includes receiving an input through a user interface of an external telemetry device, identifying an implantable medical device (IMD) type using the input, selecting at least one far-field radio frequency (RF) modulation type in the external telemetry device from a plurality of modulation types selectable in the external telemetry device using the IMD type, and modulating or demodulating one or more data signals outgoing or incoming to an IMD, using the external telemetry device and the selected modulation type.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses a field-reconfigurable RF telemetry system for bi-directional communication between a plurality of types of implantable medical devices (IMDs) and an external system. Typically, IMDs communicate wirelessly with an external device to provide bi-directional communication between the IMD and a caregiver. The communication typically follows a protocol of information transfer specified by the IMD type.

An IMD may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
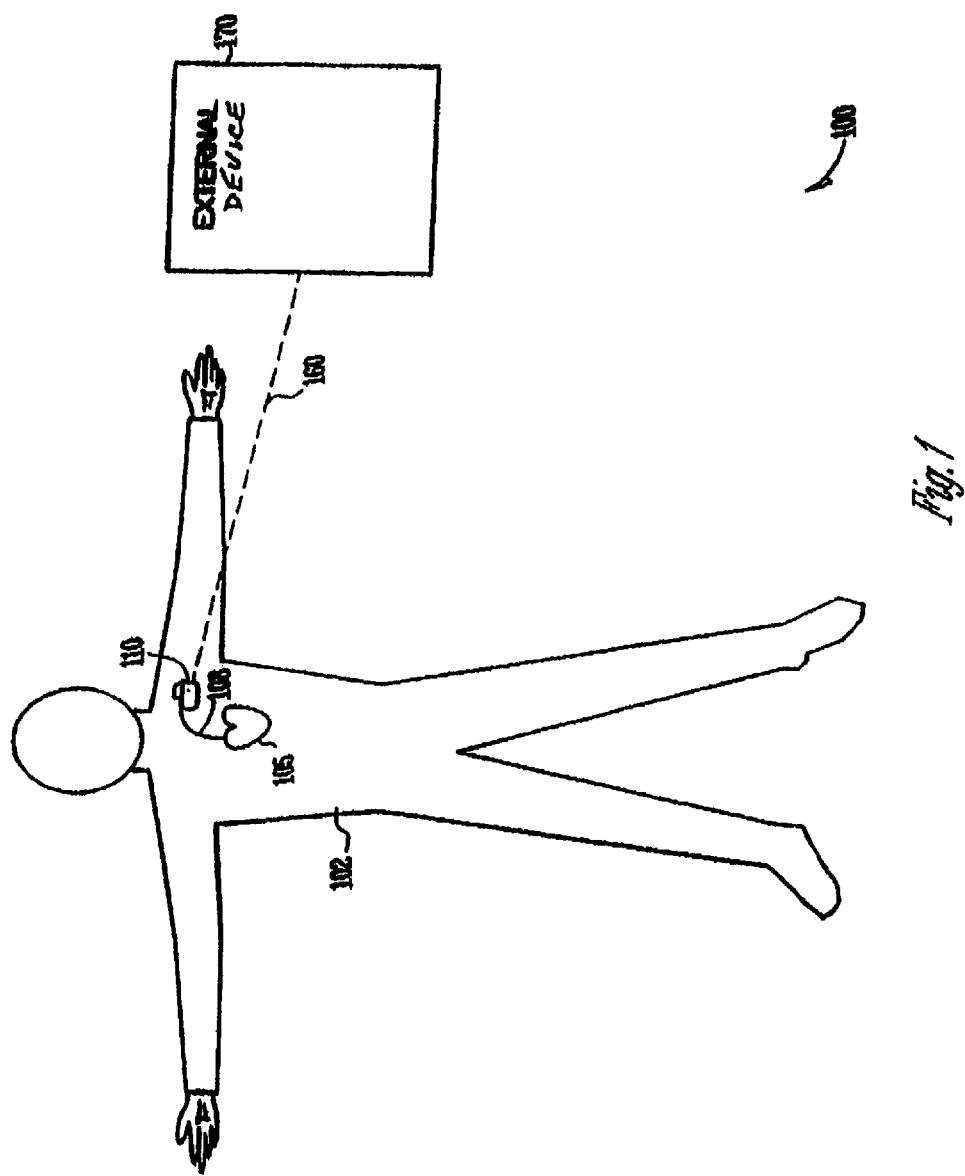
FIG. 1 is a block diagram of portions of a system that uses an implantable medical device (IMD).

FIG. 1 is a block diagram of portions of a system 100 that uses an IMD 110. As an example, the system 100 shown is used to treat a cardiac arrhythmia. The IMD 110 typically includes an electronics unit that is typically coupled by a cardiac lead 108, or additional leads, to a heart 105 of a patient 102, or otherwise associated with the heart 105. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2:
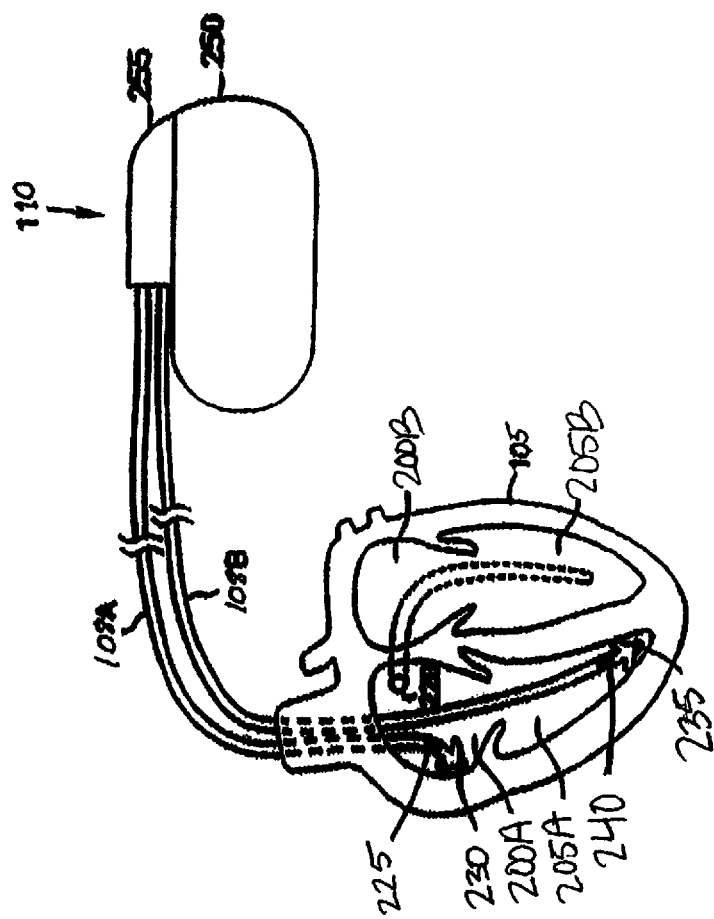
FIG. 2 illustrates an IMD coupled by one or more leads to heart.

FIG. 2 illustrates an example of an IMD 110 coupled by one or more leads 108A-C to heart 105. Heart 105 includes a right atrium 200A, a left atrium 200B, a right ventricle 205A, a left ventricle 205B, and a coronary sinus 220 extending from right atrium 200A. Atrial lead 108A includes electrodes (electrical contacts, such as ring electrode 225 and tip electrode 230) disposed in an atrium 200A of heart 105 for sensing signals, or delivering pacing therapy, or both, to the atrium 200A.

Ventricular lead 108A includes one or more electrodes, such as tip electrode 235 and ring electrode 240, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such defibrillation electrodes typically have larger surface areas than pacing electrodes in order to handle the larger energies involved in defibrillation. Lead 108B optionally provides resynchronization therapy to the heart 105.

In some examples, leads 108A and 108B are combined into one lead containing four electrodes located sequentially along the lead. In an example, a first tip electrode is located in the apex of the right ventricle 205A, a first ring electrode located proximal to the tip electrode and in the right ventricle 205A, a second ring electrode located proximal to the first ring electrode and in the right atrium 200A, and a third ring electrode located proximal to the second ring electrode and also located in the right atrium 200A.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes.

Figure 3:
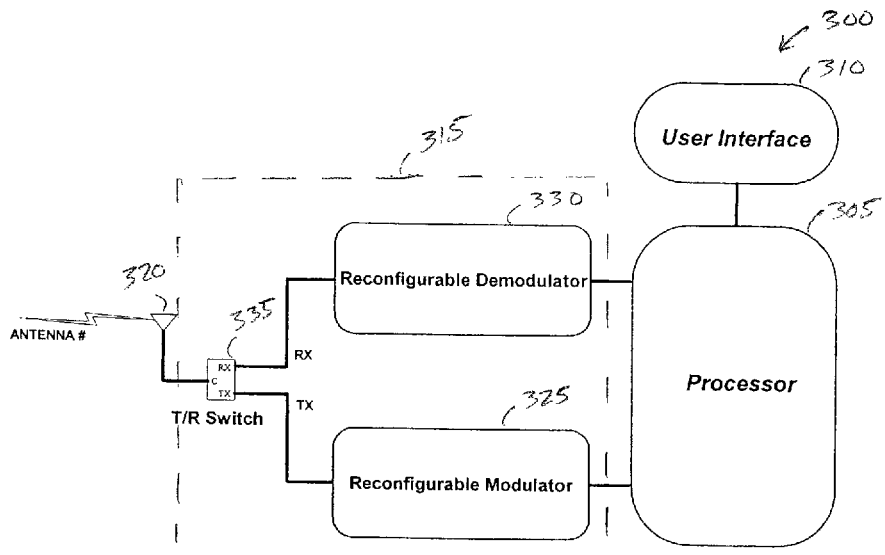
FIG. 3 is a block diagram of portions of an example of an external telemetry device that includes a field-reconfigurable RF telemetry system.

FIG. 3 is a block diagram of portions of an example of an external telemetry device 300. The external telemetry device 300 includes a processor 305, a user interface 310, and a field-reconfigurable RF telemetry system for bi-directional communication of medical data between the external telemetry device 300 and a plurality of types of IMDs. The processor 305 includes a microcontroller, a microprocessor, a digital signal processor, an application specific integrated circuit (ASIC), a field programmable gate array (FPGA), or any combination thereof. The user interface 310 is any interface circuit or circuits that allow a "user" to interact with the processor. Examples include, without limitation, a keyboard, a computer mouse, or a touch-screen. The user of a device refers to anyone who interacts with the device and includes a patient, a caregiver and a manufacturer of the device. The user interface 310 also includes a display to provide information to a user.

In some examples, the external telemetry device 300 is an IMD programmer that is able to communicate with a plurality of IMD types. In some examples, the external telemetry device 300 is a patient data display device that is able to retrieve information from a plurality of IMD types. In some examples, the external telemetry device 300 is a patient activator that allows a patient to activate an implantable device, a patient data display that reads and displays information read from the IMD. In some examples, the external telemetry device 300 is an RF repeater that communicates information over a network, such as with a server, and locally communicates information with the IMD.

Additionally, the external telemetry device 300 also includes a physical layer as part of, or in electrical communication with, the processor. The term electrical communication refers to devices arranged to communicate using electrical signals that influence the operation of the devices. In some examples, the devices are coupled directly. In some examples, the devices communicate electrical signals through intermediate devices, such as devices that include digital or analog circuits.

The physical layer includes the reconfigurable radio-frequency (RF) transceiver circuit 315 and at least one far-field antenna 320 in electrical communication with the reconfigurable RF transceiver circuit 315 through a transmit and receive (T/R) switch 335 or an RF multiplexer. The far field antenna 320 provides bidirectional RF wireless communication with an IMD according to an RF modulation type that is selectable by the processor 305 from among a plurality of modulation techniques. In the example in FIG. 3, the reconfigurable RF transceiver circuit 315 includes a configurable modulator 325 to modulate outgoing IMD data signals and a configurable demodulator 330 to detect and demodulate incoming IMD data signals. In some examples, the outgoing IMD data signals are modulated using a first modulation type and the incoming signals are demodulated with a second modulation type. In some examples, some of the functions of the physical layer are performed by the processor 305.

Figure 4A:
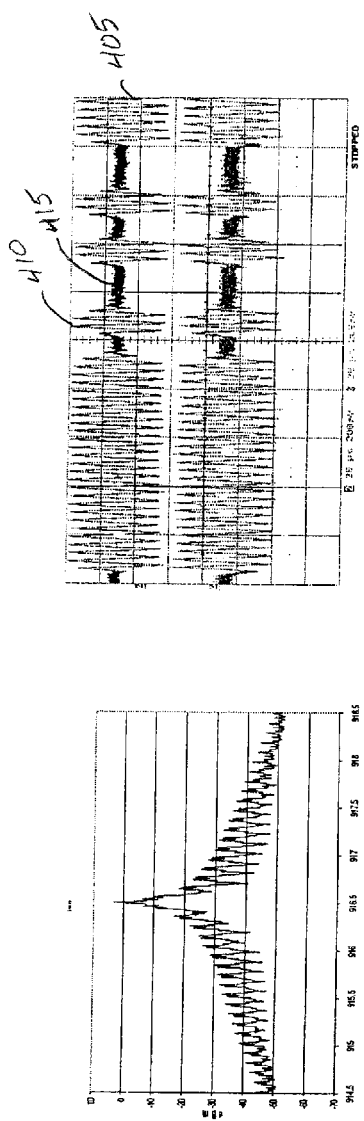
FIGS. 4A-C are graphs showing examples of types of data modulation.

In some examples, the modulation types include amplitude-shift-keying (ASK) modulation and frequency-shift-keying (FSK) modulation. An example of ASK modulation is shown in the graph 405 of FIG. 4A. In ASK modulation, a carrier frequency has a first amplitude 410 to transmit a "one" and a second amplitude 415 to transmit a "zero." In some examples, the external telemetry device 300 implements the specific ASK modulation of On-Key Off-Key (OOK) modulation. In OOK modulation the carrier frequency is multiplied by the digital signal (i.e., a one or a zero) and results in the carrier frequency being present for a one bit and absent for a zero bit.

Figure 4B:
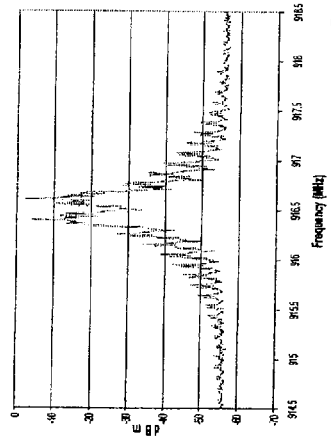

An example of FSK modulation is shown in the graph 425 of FIG. 4B. In FSK modulation, a first carrier frequency 430 is used for a one and a second carrier frequency 435 is used for a zero. If only two frequencies are used it is sometimes called binary FSK or BFSK. If four frequencies are used it is sometimes called 4-FSK or QFSK. FSK also includes any FSK produced as a result of Gaussian filtering of the binary modulation (GFSK).

Figure 4C:
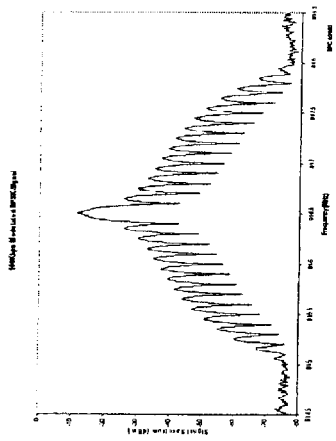

In some examples, the modulation types include phase-shift-keying (PSK) modulation. An example of PSK modulation is shown in the graph 445 of FIG. 4C. In PSK modulation, a first phase of the carrier 450 is used for a one and a second phase 455 is used for a zero. PSK includes binary phase-shift-keying (BPSK) modulation that has only two phases; zero and r. PSK also includes quadrature phase-shift-keying (QPSK) modulation that has four phases; zero, $\pi/2$, $\pi$, and $3\pi/2$. In some examples, the reconfigurable RF transceiver circuit 415 can be configured to modulate and demodulate incoming and outgoing IMD data signals using a modulation type that modulates both amplitude and phase of data signals such as quadrature amplitude modulation (QAM), or using minimum shift-keying (MSK) which is a combination of PSK and FSK.

In some examples, the modulation types include direct-sequence spread spectrum modulation (DSSS). In DSSS, each bit of a digital modulation is multiplied by a higher bit-rate digital sequence. In DSSS different users may coexist if they are assigned sequences from sets of codes which are orthogonal to each other. One user's signal appears as noise to the other users. In some examples, the modulation types include frequency hopped spread spectrum modulation (FHSS). In FHSS, the carrier frequency hops from one to another value in the course of communicating to mitigate interference and poor signal propagation. In some examples, the modulation includes a combination of FHSS, BFSK, and QPSK. In some examples, the modulation types include orthogonal frequency division multiplexing (OFDM). In OFDM, a range of the frequency spectrum is subdivided into a collection of modulated subcarriers. Orthogonality ensures noninterference among the subcarriers.

Returning to FIG. 3, the reconfigurable RF transceiver circuit 315 represents any RF transceiver circuit configurable to implement two or more of any digital modulation types. In some examples, the reconfigurable RF transceiver circuit 315 can be configured to modulate and demodulate incoming and outgoing IMD data signals using any of ASK, OOK, FSK, BFSK, GFSK, QFSK, MSK, PSK, BPSK, QPSK, QAM, OFDM, FHSS, and DSSS modulation types, or any combination of the modulation types. In some examples, the modulator 325 and demodulator 330 are implemented in hardware. In some examples, they are implemented in a combination of hardware and software.

In some examples, the processor 305 selects the modulation type to be used by the reconfigurable RF transceiver circuit 315 according to information entered by a user. In some examples, the information includes an IMD type. Typically, IMDs of a certain type will follow the same communication protocol. In some cases, more than one IMD type made by a manufacturer will communicate using the same protocol. In some examples, the IMD type is provided by the user indicating an IMD model number. In some examples, the IMD type is provided by the user indicating an IMD serial number. In some examples, the IMD type is provided by the user indicating an IMD product or IMD product family using the user interface 310.

Figure 5:
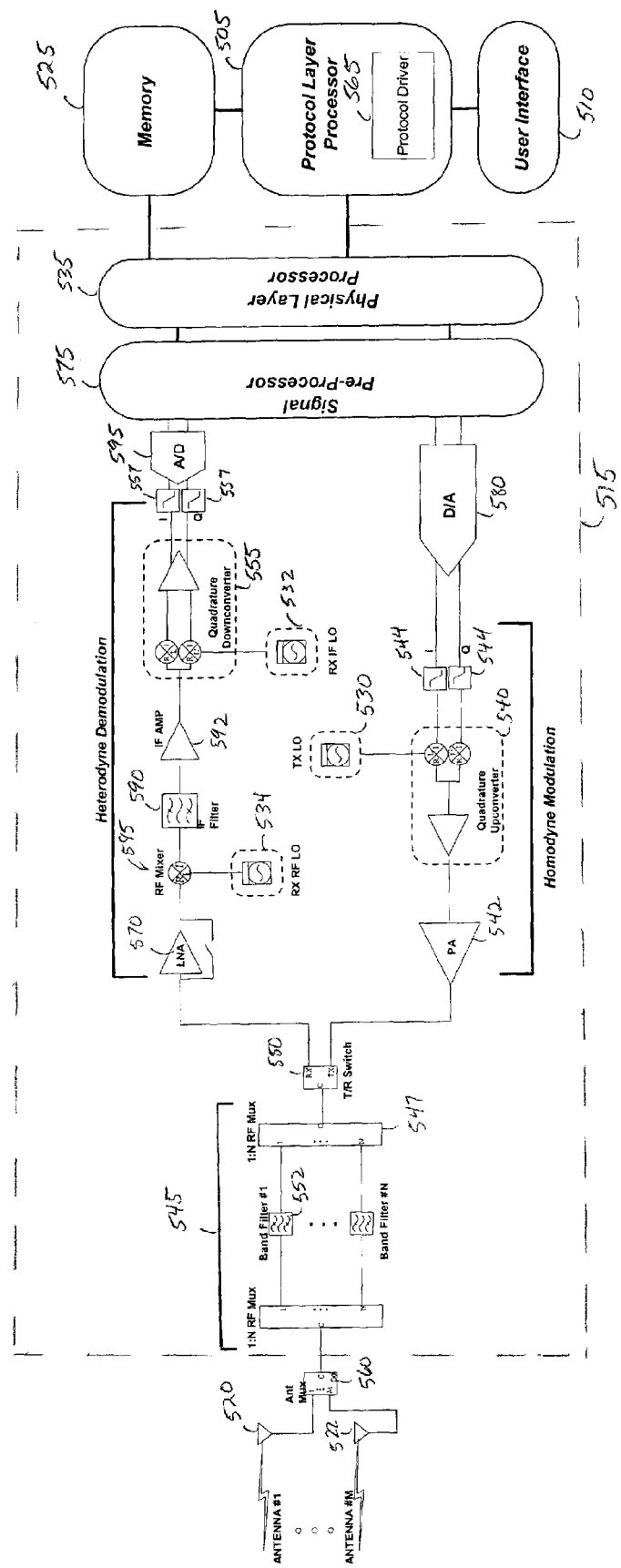
FIG. 5 is a block diagram of portions of another example of an external telemetry device that includes a field-reconfigurable RF telemetry system.

FIG. 5 is a block diagram of portions of another example of an external telemetry device 500 that includes a field-reconfigurable RF telemetry system. The external telemetry device 500 includes a user interface 510, a protocol layer, and a physical layer. The protocol layer includes a protocol layer processor 505 and a memory 525. The physical layer includes a reconfigurable RF transceiver circuit 515 and one or more antennae 520, 522.

The reconfigurable RF transceiver circuit 515 includes a physical layer processor 535 to construct a baseband transmit signal. In some examples, a single processor, such as a digital signal processor (DSP), performs the functions of both the protocol layer processor 505 and the physical layer processor 535. The physical layer processor 535 generates the signal which is passed to a signal pre-processor 575 and then to a digital-to-analog (D/A) converter stage 580. In some examples, the signal pre-processor 575 includes a reconfigurable transmit signal pre-processor described below.

In the example shown, a zero or near-zero intermediate frequency (IF) homodyne up-conversion system architecture is used. In some examples, a heterodyne architecture is used. In some examples, a direct conversion architecture is used. The quadrature up-converter 540 in the transmit signal path up-converts the baseband signal to a desired carrier frequency $f_C$ defined as:

$$f_C = f_{TXLO} \pm f_{baseband}, \quad (1)$$

where $f_{TXLO}$ is a local oscillator frequency for transmit signals and $f_{baseband}$ is the frequency of the baseband signal. A local oscillator (LO) frequency generation circuit 530 generates at least one LO frequency which, when combined with the baseband frequency is within a communication frequency allocation band. The carrier frequency and the communication frequency allocation band are selectable from a plurality of communication frequency allocation bands by the protocol layer processor 505 through the physical layer processor 535. In some examples, the communication frequency allocation band is selected according to an IMD type.

In some examples, the plurality of communication frequency allocation bands includes frequency bands allocated for wireless short range devices (SRDs). Transmissions at approved power levels at these frequencies minimize interference with other radio equipment. The reconfigurable RF transceiver circuit 515 includes an adjustable power amplifier circuit 542 to adjust the transmit power level. The communication frequency allocation bands include, among other frequency bands, the medical implant communication service (MICS) band of 402-405 MHz, the North American industrial, scientific, and medical (ISM) band of 902-928 MHz, the European (EU) short range device (SRD) bands of 434 MHz and 862-870 MHz, and the Japanese SRD bands within the range of 420 MHz-450 MHz.

The combination of the frequency generation circuit 530 output with the baseband frequency generate carrier frequencies, or channels, having adequate separation from other carrier frequencies within the communication frequency allocation bands. The channels within the bands are selectable by the physical layer processor 535. In some examples, the channels within the bands are selectable by the protocol layer processor 505 through the physical layer processor 535. In some examples, the carrier frequency is selected according to an IMD type indicated by the user interface 510.

Figure 6:
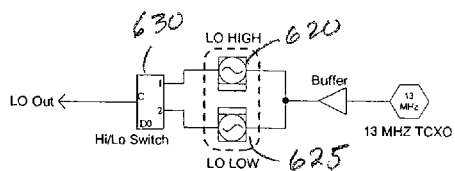
FIG. 6 is a block diagram of portions of a local oscillator frequency generation circuit.

FIG. 6 is a block diagram of portions of a LO frequency generation circuit 600. The Figure shows the simple case of selecting between two carrier frequency ranges which together provide all communication frequency allocation bands. A first signal generator 620 generates a local oscillator (LO) signal with a frequency $f_{c1}$ that is programmable from 862 MHz to 928 MHz. This range includes the North American ISM band and part of the European SRD band. A second signal generator 625 generates an LO signal with a frequency $f_{c2}$ that is programmable from 402 MHz to 440 MHz. This range includes the MICS band, the Japanese SRD band, and part of the EU SRD band. The LO frequency from a signal generator 620, 625 is selected by a switch 630 or multiplexer.

Returning to FIG. 5, a complex differential baseband signal (TXI, TXQ) is created for the transmit signal path. The baseband signal is filtered by low pass filters 544 before entering a quadrature up-converter 540. In some examples, the signals enter an image reject mixer instead of a quadrature up-converter 540. The low pass filters 544 narrow the bandwidth of the transmit signal and remove higher harmonic frequencies resulting from the D/A conversion (sometimes called "D/A spurs"). The image reject mixer or the quadrature up-converter 540 combines the baseband signal with the selected LO frequency to generate the carrier frequency as described in equation (1).

The reconfigurable RF transceiver circuit 515 also includes a programmable filter 545 in electrical communication with the power amplifier 542 through a transmit-receive (T/R) switch 550 or an RF multiplexer. The programmable filter 545 filters outgoing modulated IMD data signals and filters incoming modulated IMD data signals. One of a plurality of band filters 552 is selected by the physical layer processor 535 using RF switches 547 or multiplexes. In some examples, the individually selectable band filters 552 include surface acoustic wave (SAW) filters. In some examples, one of the filters 552 is an all-pass filter. The programmable band filter 545 includes N such filters corresponding to at least a portion of the selectable communication frequency allocation bands.

In some examples, one of the N band filters 552 is selected based upon the communication frequency allocation band selected. In some examples, one of the N band filters 552 is selected according to the IMD type indicated by the user interface 510. In some examples, one of the N band filters 552 is selected according to a geographic location where the programmer is used. The geographic information is provided through the user interface.

The physical layer also includes one or more far-field antennae 520, 522. When more than one antenna is included, an antenna control circuit 560 is arranged between the reconfigurable RF transceiver circuit 515 and the antennae 520, 522. In some examples, a first antenna 520 is a horizontal printed dipole antenna enclosed within a housing of the external telemetry device 500, and a second antenna 522 is a vertical dipole antenna mounted external to the housing.

The two or more far field antennae 520, 522 form a diverse antenna system. Far-field RF telemetry between an IMD and the external device 500 may operate in an environment where RF electromagnetic waves are reflected from various kinds of surfaces. Destructive interference between the incident and reflective waves results in nulls, where an incident wave and a reflected wave cancel out. The far-field RF telemetry link can be substantially interrupted when an antenna encounters a null. While such a null is moving and usually transient, the interruption to the telemetry link may last long enough to cause a data transmission error.

The antenna control circuit 560 is configured by the physical layer processor 535 which uses receive signal information to detect a signal transmission failure from one antenna and to electrically connect a second antenna to the reconfigurable RF transceiver circuit in response to one or more signal transmission failures. Descriptions of apparatuses for antenna selection in a diversity antenna system are found in commonly assigned U.S. patent application Ser. No. 11/068,478 entitled, "METHOD AND APPARATUS FOR ANTENNA SELECTION IN A DIVERSITY ANTENNA SYSTEM FOR COMMUNICATING WITH IMPLANTABLE MEDICAL DEVICE," filed on Feb. 28, 2005, which is hereby incorporated by reference.

In some examples, the reconfigurable RF transceiver circuit 515 includes an adjustable receive sensitivity circuit 570. The sensitivity level of the receive signal is adjusted by programming an amount of gain on the received signal path. The gain is adjusted by adjusting a gain range of gain stage blocks and by removing or adding the gain stage blocks themselves. In some examples, the protocol layer processor 505 automatically adjusts the receive sensitivity level of the reconfigurable RF transceiver circuit according to the IMD type communicated to the protocol layer processor 505. In some examples, the gain of the receive signal is adjusted using an analog automatic gain control (AGC) circuit which measures received signal strength and tries to keep received signals at a constant amplitude. In some examples, the transmit power of outgoing signals is adjusted based on the measured received signal strength. If a received signal measurement circuit, such as an AGC for example, indicates that the received signal strength is high, the external telemetry device 500 can decrease transmit power to reduce possible interference with other nearby devices. Conversely, if the received signal strength is low, the external telemetry device 500 can increase transmit power to maintain communication with the IMD.

In the example shown, the reconfigurable RF transceiver circuit 515 uses a heterodyne architecture for an RF receiver. In some examples, a zero or near-zero intermediate frequency (homodyne) architecture is used for an RF receiver. In some examples, a direct conversion architecture is used for an RF receiver.

The RF receiver includes an RF mixer 585, receive RF LO frequency generation circuit 534, intermediate frequency (IF) filter 590, intermediate frequency amplifier 592, a quadrature down-converter 555, receive IF LO frequency generation circuit 534, baseband filters 544, and an analog to digital converter 595. The local oscillators 532, 534 are configurable. An advantage of the heterodyne architecture is that the IF filter 590 improves the noise and image rejection of the RF receiver. The RF mixer 585 and a quadrature down-converter 555 down-convert and demodulate incoming RF IMD data signals to baseband signals of intermediate frequency. In an illustrative example, the intermediate frequency is 2 MHz. The signals on the in-phase (I) and in-quadrature (Q) receive paths are then low pass filtered with baseband filters 544. In some examples, the baseband filters 544 are seventh order elliptical low pass filters.

In some examples, the RF receiver also includes a reconfigurable receive signal pre-processor within the signal pre-processor 575. The reconfigurable receive signal pre-processor provides channel filtering and the final quadrature down-conversion.

Figure 7:
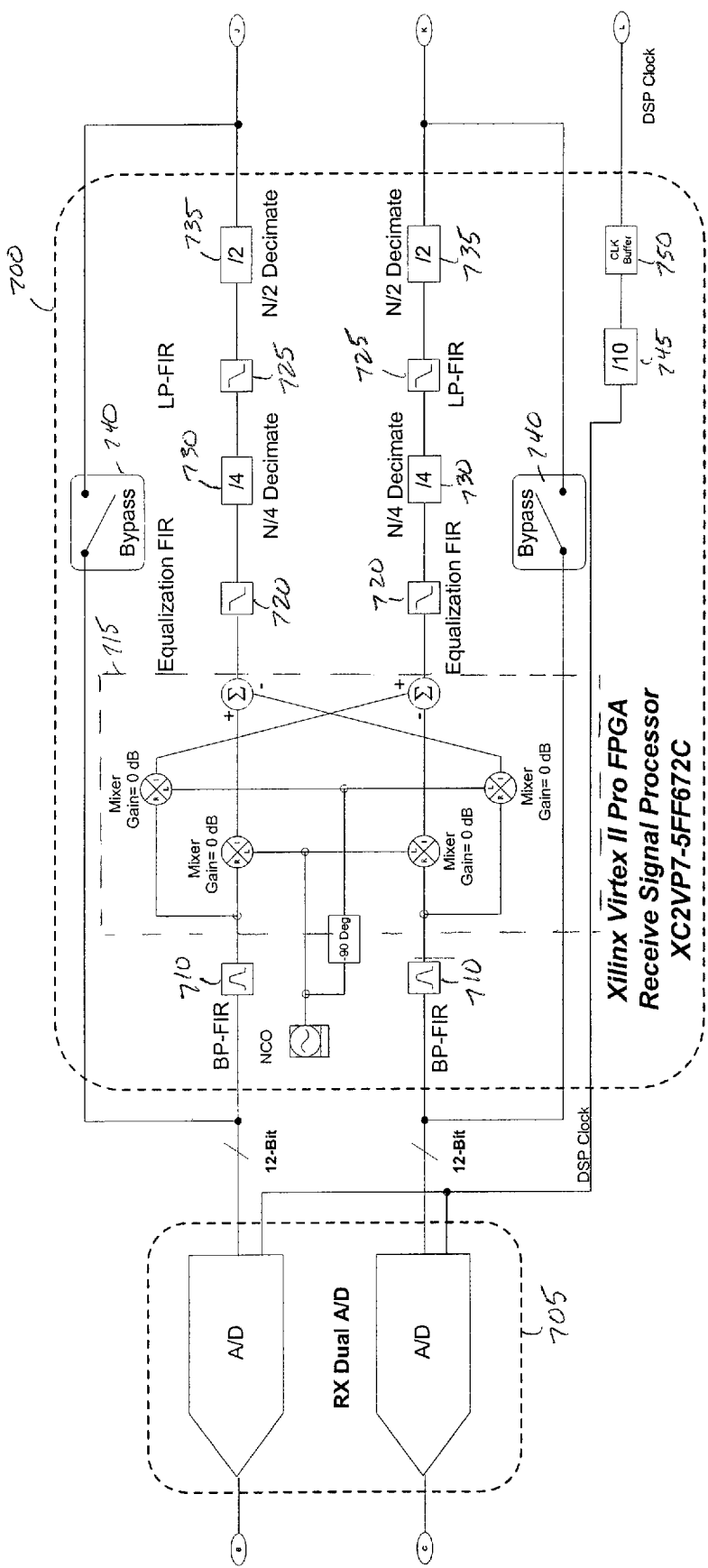
FIG. 7 is a block diagram of portions of an example of a reconfigurable receive signal pre-processor.

FIG. 7 is a block diagram of portions of an example of a reconfigurable receive signal pre-processor 700. In some examples, the reconfigurable receive signal pre-processor 700 is implemented using a field programmable gate array (FPGA). The signals on the I and Q receive paths are converted to digital signals using the analog-to-digital (A/D) converters 705. In some examples, the reconfigurable receive signal pre-processor 700 is bypassed in the receive signal path using bypass switches 740. In examples that include a DSP, the clock buffer 750 and clock divider 745 divide the DSP clock down to a programmable lower frequency at the A/D 705.

The reconfigurable receive signal pre-processor 700 includes a bandpass filter stage to band limit signals on the I and Q channels which improves the signal-to-noise ratio. In some examples, the bandpass filters 710 include seventy-three tap finite impulse response (FIR) filters with programmable coefficients. The parameters of the bandpass filters 710 are configurable, and are chosen based on the carrier frequency and the data rate of the incoming IMD data signals. For example, if a selected incoming data signal converts down to a baseband frequency of 2.0 MHz, the center frequency will be chosen to be 2.0 MHz and the bandwidth will be chosen to be 800 kHz if its minimum ASK data rate was 400 kbps or less. In some examples, the parameters are configured according to an IMD type. In some examples, the bandpass filters 710 are configured to be Kaiser-type filter with a critical frequency of 750 kHz and a bandwidth of 500 kHz.

The reconfigurable receive signal filter 700 includes an image reject down-conversion stage 715 for image rejection. The down-conversion mixing function shifts the desired signal and attenuates the image signal to provide additional separation between the signals. In the example of a 2.0 MHz baseband frequency, the desired signal is shifted to 600 kHz and the image signal is shifted to 3.4 MHz. The reconfigurable receive signal filter 700 includes low pass filter stages 720, 725 to attenuate the shifted image signal further. In some examples, the low pass filters 720, 725 include seventeen tap FIR filters with programmable coefficients. In some examples, the low pass filters 720, 725 are Kaiser-type type filters with a critical frequency of 500 kHz. The decimation stages 730, 735 reduce the number of digitized samples provided to the physical layer processor for data recovery. In some examples, the reconfigurable receive signal filter 700 includes additional notch filters for interference rejection. Bypass switches 740 allow the reconfigurable receive signal filter 700 to be bypassed in the receive signal path.

Returning to FIG. 5, after the signal pre-processor 575 optionally processes the incoming data signals with the reconfigurable receive signal filter, the physical layer processor 535 demodulates the signals and assembles the data into frames to be stored in the protocol layer memory 525.

Figure 8:
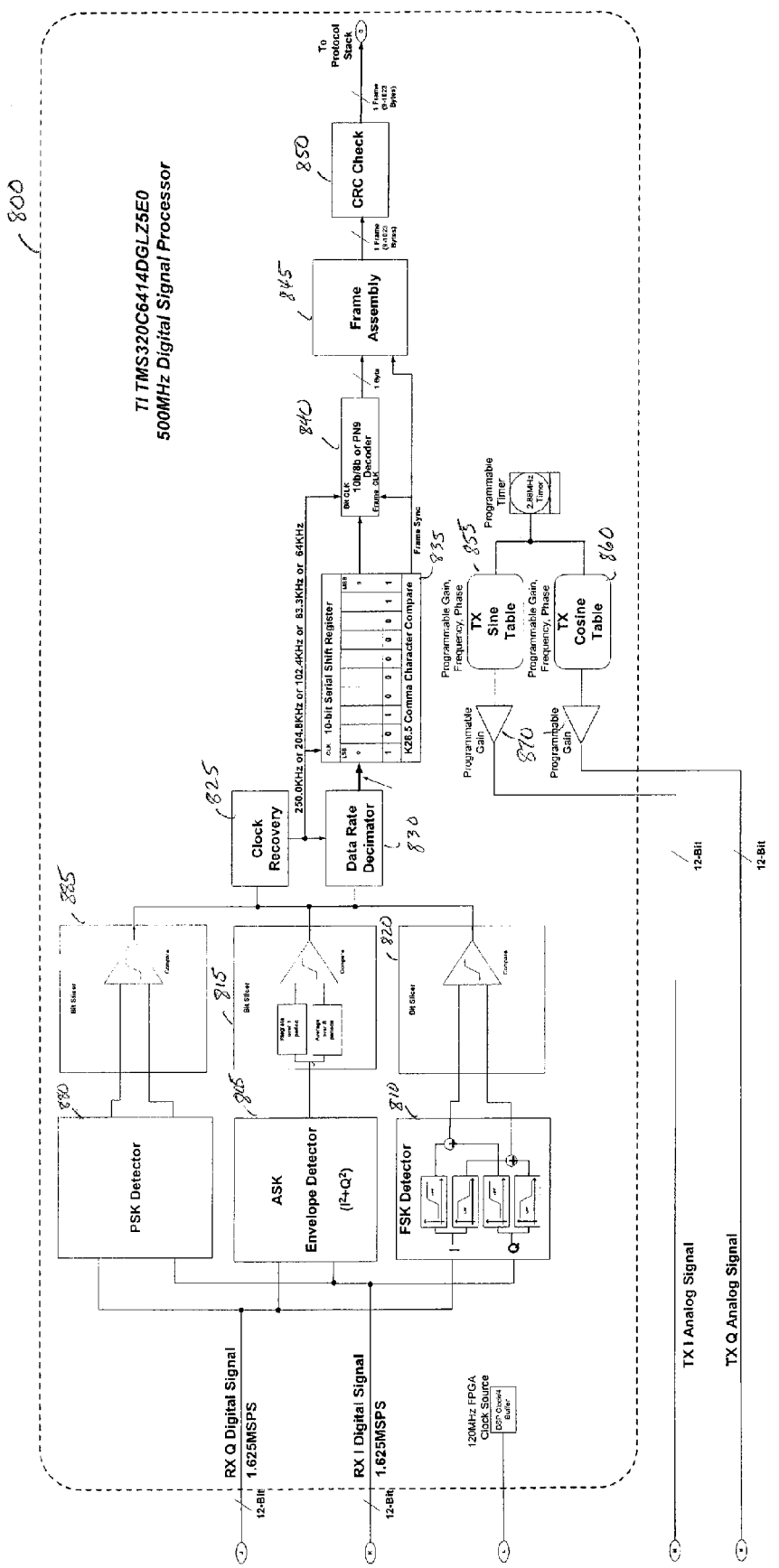
FIG. 8 is a block diagram of portions of an example of a physical layer processor.

FIG. 8 shows a block diagram of portions of an example of a physical layer processor 800. In some examples, the functions of the physical layer processor 800 and the protocol layer processor are performed by a single processor, such as a DSP. The physical layer processor 800 assembles received data into frames and disassembles frames for transmission of data. Incoming IMD data signals are received at a modulation detector 805, 810, 880. The example shows that the physical layer processor 800 is configurable between an ASK modulation detector 805, an FSK modulation detector 810, and a PSK modulation detector 880, but the physical layer processor 800 can be configured to include detectors for any combination of the modulation methods discussed previously. The modulation detectors 805, 810, 880 can be implemented in a combination of hardware and software modules executing in the physical layer processor 800. In some examples, the modulation detectors 805, 810, 880 are implemented in firmware on a DSP.

The physical layer processor 800 includes a bit slicer circuit 815, 820, 885, a clock recovery circuit 825, and a data rate decimator circuit 830 to extract the individual data bits from the modulated signals. The physical layer processor 800 is programmable to receive modulated data or transmit modulated data at a plurality of data rates. In some examples, the physical layer processor 800 is programmable to receive modulated data or transmit modulated data between 63.3 kHz to 250 kHz. In some examples, the physical layer processor 800 is programmable to receive modulated data or transmit modulated data at predetermined rates. In an illustrative example, the predetermined rates include 63.3 kHz, 85.3 kHz, 102.4 kHz, 204.8 kHz, and 250 kHz. The receive data rate and the transmit data rate do not have to be equal. In another illustrative example, the receive data rate is 204.8 kHz and the transmit data rate is 102.4 kHz. In some examples, the receive data rate and transmit data rate are selected according to an IMD type communicating the incoming IMD data signals. In some examples, the IMD type is communicated to a protocol layer processor from a user interface, and the protocol layer processor selects the receive data rate based on the IMD type.

The physical layer processor 800 includes a shift register 835 and decoder 840 to receive the demodulated data. The demodulated data is assembled into frames in the frame assembly registers 845 and the CRC of the data transmission is monitored using a CRC circuit 850. Bytes of data are sent to the protocol layer memory.

To transmit data, the physical layer processor 800 retrieves bytes of data from the protocol layer memory 525. The bytes of data are disassembled into individual bits for modulation. The physical layer processor 800 constructs a complex quadrature baseband signal using a sine lookup table 855 and a cosine lookup table 860. The generated sine and cosine waves have amplitude, frequency, and phase programmable by the physical layer processor 800. In some examples, the amplitude, frequency, and phase of the generated sine and cosine waves are selected by the protocol layer processor based on a type of IMD with which the external telemetry device 500 is communicating.

The physical layer processor 800 is configurable to transmit outgoing data at a plurality of data rates. The transmit data rate is selectable from a plurality of data rates according to the IMD type. In some examples, the IMD type is communicated to the protocol layer processor, which selects the data rate in the physical layer processor 800. The physical layer processor 800 modulates the transmit data at the plurality of data rates using the generated sine and cosine waves. The amplitude, frequency, and phase of the outgoing data signals are selected according to the modulation type used by the indicated IMD type.

Figure 9A:
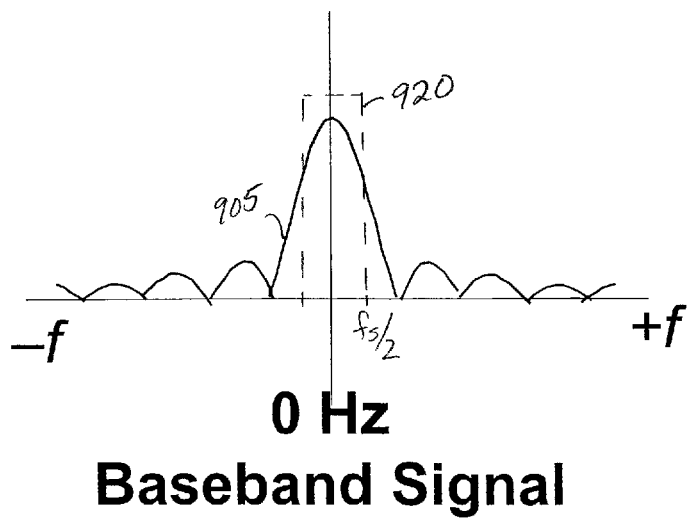
FIGS. 9A-C are graphical illustrations of the frequency spectrum of a baseband signal and filtering concerns related to the frequency spectrum.
Figure 9B:
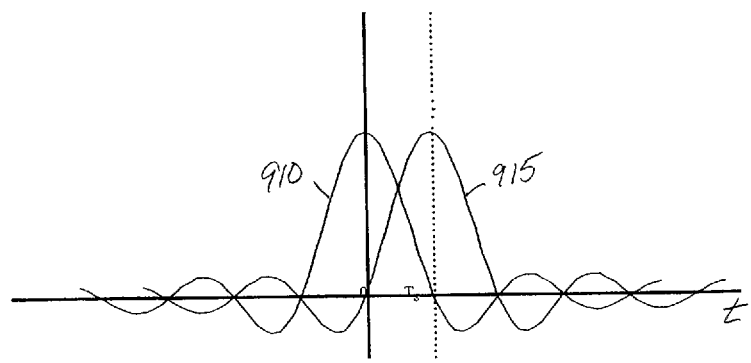

According to some examples, the physical layer processor 800 includes amplifiers 870 that provide programmable gain to the outgoing data signals. In some examples, the physical processor 800 includes a programmable wave-shaping module in electrical communication with the programmable gain amplifiers 870 to wave-shape an outgoing modulated carrier signal according to one of a plurality of wave-shaping functions. This wave-shaping is sometimes referred to as RF pulse-shaping. FIG. 9A shows an illustration of the frequency spectrum 905 of a baseband signal. FIG. 9B shows the frequency spectrum of two RF symbols 910, 915 superimposed on a time domain axis. The graph shows that if a second symbol 915 is transmitted too close to a first symbol 910, the response of the first symbol 910 may interfere with the second symbol 915. Thus, wave-shaping is performed to narrow the bandwidth of the transmitted RF symbols to minimize inter-symbol interference.

A perfect low pass filter with a bandwidth of one-half the symbol frequency $f_s/2$ would prevent inter-symbol interference. However, such a low pass filter is not practical. FIG. 9A shows a passband 920 for the ideal "brick wall" filter. Filters can be described in terms of a design parameter a to describe the sharpness of the filter. The bandwidth BW is approximately $$BW = f_s \cdot (1+\alpha) \qquad (2).$$

Figure 9C:
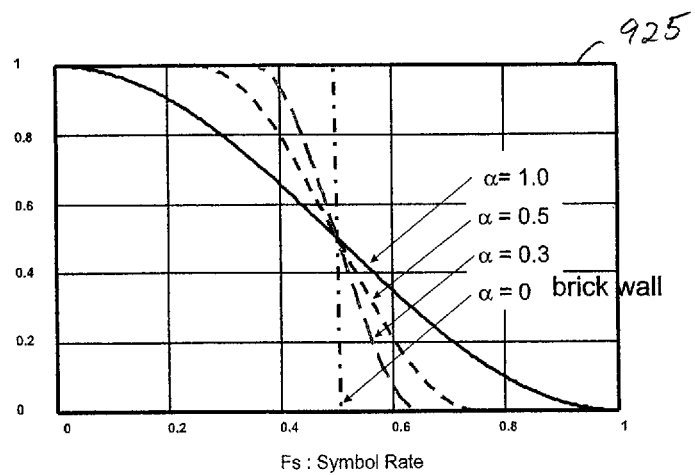

FIG. 9C shows graphs 925 of a low pass filter response as a function of $\alpha$. The graphs 925 show that $\alpha=0$ corresponds to the ideal filter. The sharpness of the filter decreases as $\alpha$ varies from 0.0 to 1.0. A typical value for a wave-shaping filter function is $\alpha=0.3$ to 0.35. In some examples, the wave-shaping function is an FIR filter function or module implemented in the physical layer processor 800 of FIG. 8.

In some examples, the protocol layer processor is adapted to select a wave-shaping function for the outgoing modulated carrier signal according to the IMD type communicated to the protocol layer processor. In some examples, the wave-shaping function includes additional low pass filters (placed before the D/A converter 580 in FIG. 5) to further narrow the bandwidth of the transmit signals.

Returning to FIG. 5, the programmable power amplifier 542 implements a coarse adjustable transmit power circuit. In some examples, the programmable gain provided by the amplifier allows the transmit power to be reduced from −30 decibels (dB) to 0 dB in steps less than or equal to 2 dB over all frequency bands. In some examples, the physical layer processor 535 automatically adjusts the coarse transmit power of the reconfigurable RF transceiver circuit according to the IMD type communicated to the protocol layer processor. In some examples, the physical layer processor 535 automatically adjusts the coarse transmit power of the reconfigurable RF transceiver circuit according to geographic location information communicated to the protocol layer processor.

Figure 10:
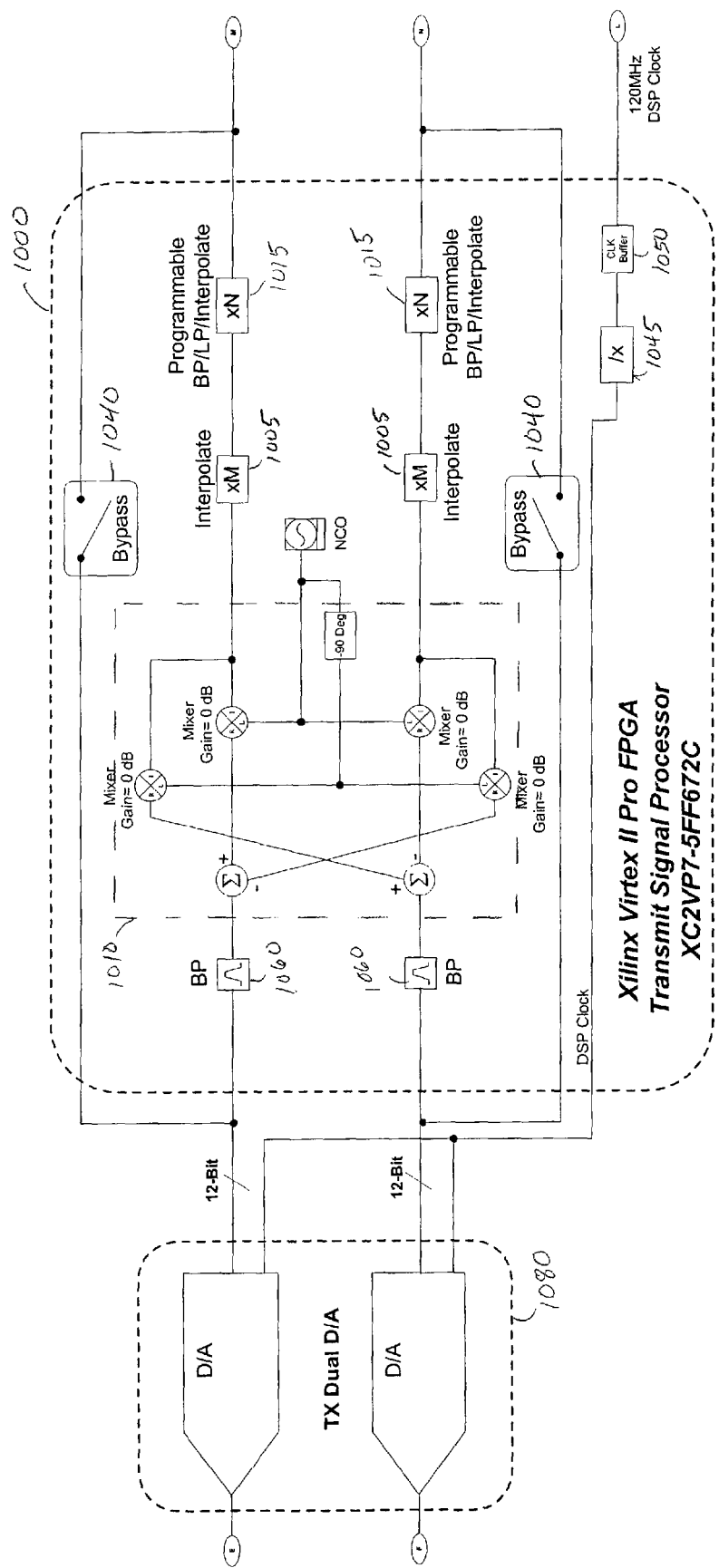
FIG. 10 is a block diagram of portions of an example of a reconfigurable transmit signal pre-processor.

In some examples, the signal pre-processor 575 includes a reconfigurable transmit signal pre-processor. FIG. 10 is a block diagram of portions of an example of a reconfigurable transmit signal pre-processor 1000. In some examples, the reconfigurable transmit signal pre-processor 1000 is implemented using an FPGA. The reconfigurable transmit signal pre-processor 1000 includes bandpass filters 1060 and programmable band-pass/low-pass (BP/LP) FIR filters 1015 followed by programmable interpolation filters 1005. The BP/LP FIR filters 1015 reduce signal noise. The interpolating filters 1005 up-sample the signal to improve timing resolution and allow for frequency up-conversion. In some examples, the reconfigurable transmit signal pre-processor 1000 includes a wave-shaping module. In some examples, the reconfigurable transmit signal pre-processor 1000 includes a state machine that modulates outgoing IMD digital data according to selectable modulation types (e.g. ASK, OOK, FSK, BFSK, GFSK, QFSK, MSK, PSK, BPSK, QPSK, QAM, OFDM, FHSS, and DSSS). This offloads the modulation function from the physical layer processor. In some examples, the reconfigurable transmit signal pre-processor 1000 includes an image rejection mixer 1010 to perform carrier frequency translation prior to transferring the digital data to the D/A converter 1080. In some examples, the reconfigurable transmit signal pre-processor 1000 is bypassed in the receive signal path using bypass switches 1040. In examples that include a DSP, the clock buffer 1050 and clock divider 1045 divide the DSP clock down to a programmable lower frequency at the D/A 1080.

Returning to FIG. 5, the protocol layer memory 525 stores frames of data received from the physical layer processor 535 and stores frames of data for transmission by the physical layer. The frames of data are sent to the physical layer processor 535 where they are disassembled into data bits for modulation and transmission.

According to some examples, the protocol layer includes a plurality of protocol drivers 565. A protocol driver 565 defines the content and order of the bytes of data stored into the protocol layer memory 525 for transmission to an IMD by the physical layer and received by the physical layer from an IMD. This order is typically determined by a manufacturer's proprietary protocol followed by an IMD type. Thus, the protocol driver 565 manages information at a byte level in the protocol layer and leaves the transmitting and receiving of individual bits to the physical layer. In some examples, the protocol drivers also include parameters communicated to the physical layer processor 535 to configure the RF transceiver circuit 515.

In some examples, the protocol drivers 565 are stored in the protocol layer memory 525 and in some examples, the protocol drivers 565 are stored in a different memory, such as a memory included in the protocol layer processor 505. The protocol layer processor 505 enables loading one of the protocol drivers 565 for execution on the protocol layer processor 505. In some examples, the protocol layer processor 505 enables loading of one of the plurality of protocol drivers 565 into a protocol layer processor memory according to the IMD type. The protocol layer then communicates information with the IMD by storing frames of data in the protocol layer memory 525 for transmission to the IMD and reading frames of data received by the IMD from the protocol layer memory 525 according to a protocol driver 565.

According to some examples, the protocol drivers 565 include one or more drivers to enable the external telemetry device 500 to communicate with a second external device. In some examples, the second device is manufacturer's device, such as a telemetry repeater for example. The second device may follow a manufacturer's proprietary protocol. In some examples, the second device does not follow a proprietary protocol.

In some examples, the protocol layer of the external telemetry device 500 includes a MAC layer and a protocol driver 565 that enables the external telemetry device 500 to communicate with a device that follows at least one of the IEEE standard 802.11 family of protocols, such as over a wireless local area network (WLAN). In some examples, the external telemetry device 500 includes a third antenna dedicated for communication using the WLAN. Loading and executing the protocol driver 565 that follows such a standard also configures the physical layer of the external telemetry device 500 by any of the methods discussed previously to modulate outgoing data signals and receive and demodulate incoming data signals according to the standard. This allows the external telemetry device 500 to communicate with non-medical devices such as printers, servers, or computer networks.

In some examples, the protocol layer of the external telemetry device 500 includes a protocol driver 565 that enables the external telemetry device 500 to communicate with a device that follows the Bluetooth™ wireless protocol. In some examples, the protocol layer of the external telemetry device 500 includes a protocol driver 565 that enables the external telemetry device 500 to communicate with a device that follows the ZigBee protocol. Loading and executing a protocol driver 565 that follows either of these standards also configures the physical layer of the external telemetry device 500 by any of the methods discussed previously to modulate outgoing data signals and receive and demodulate incoming data signals according to the Bluetooth™ protocol or the ZigBee protocol.

Figure 11:
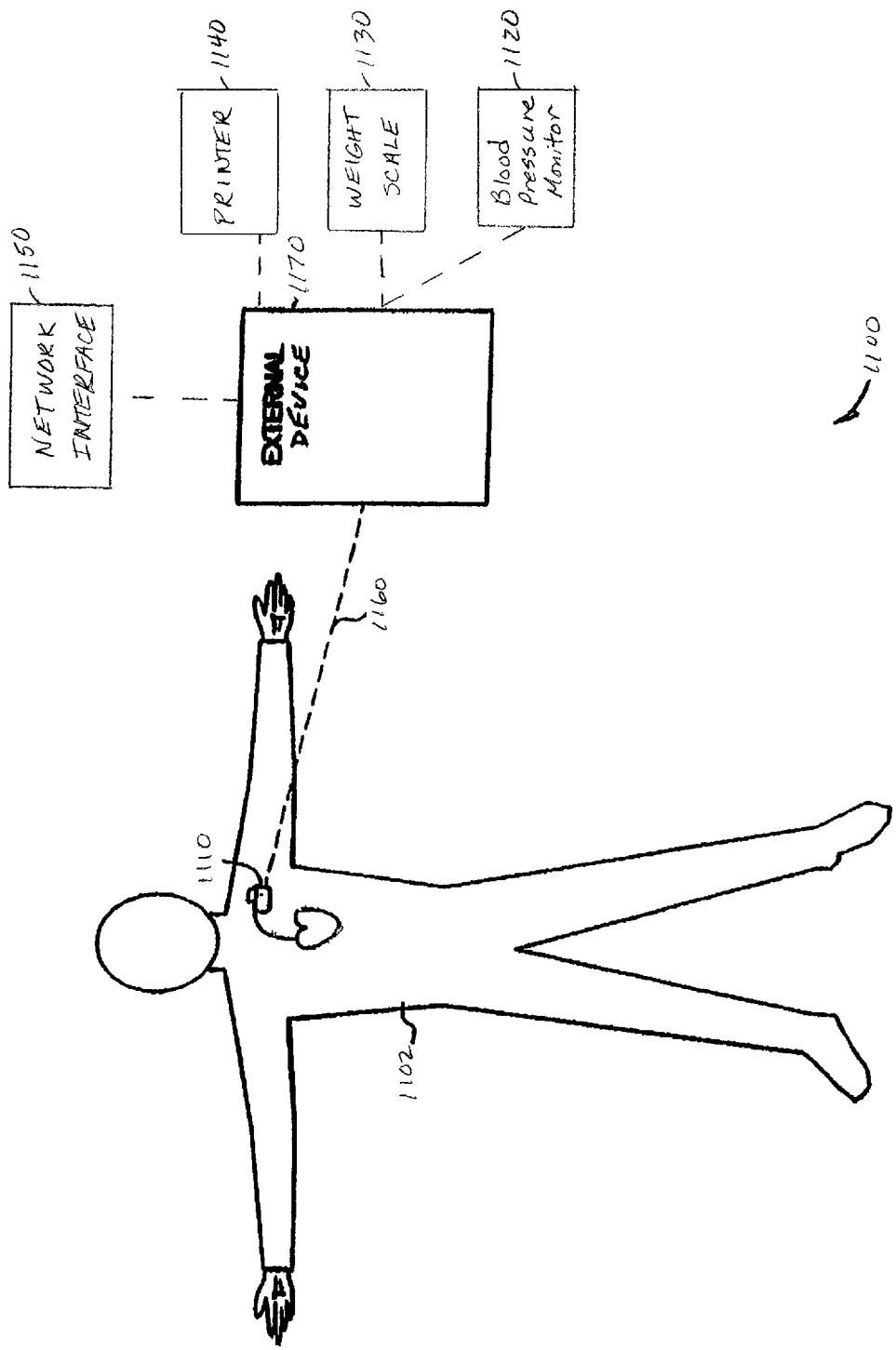
FIG. 11 is a block diagram of portions of a system that includes an IMD, an external telemetry device, and other external devices.

FIG. 11 is a block diagram of portions of a system 1100 that includes an IMD 1110 and an external telemetry device 1170 that communicates wireless signals 1160 with the IMD 1110 of a subject 1102 and with other external devices. In some examples, the external telemetry device 1170 communicates wirelessly with an interface 1150 to a network using a WLAN protocol such as the IEEE standard 802.11 family of protocols for example. In some examples, the external telemetry device 1170 communicates wirelessly with a printer using a WLAN protocol or the Bluetooth™ protocol. In some examples, the external telemetry device 1170 communicates wirelessly with a weight scale 1130 and a blood pressure monitor 1120 using the Bluetooth™ protocol. In some examples, the external telemetry device 1170 communicates with other medical devices using proprietary protocols.

Many different functional blocks have been described. In some examples of the external telemetry device 500, functions performed by individual blocks can be moved from one block to another and still be within the scope of the examples. For instance, functions performed by the physical layer processor 535 can be moved into the signal pre-processor 575; particularly if the signal pre-processor 575 is implemented in an FPGA.

Figure 12:
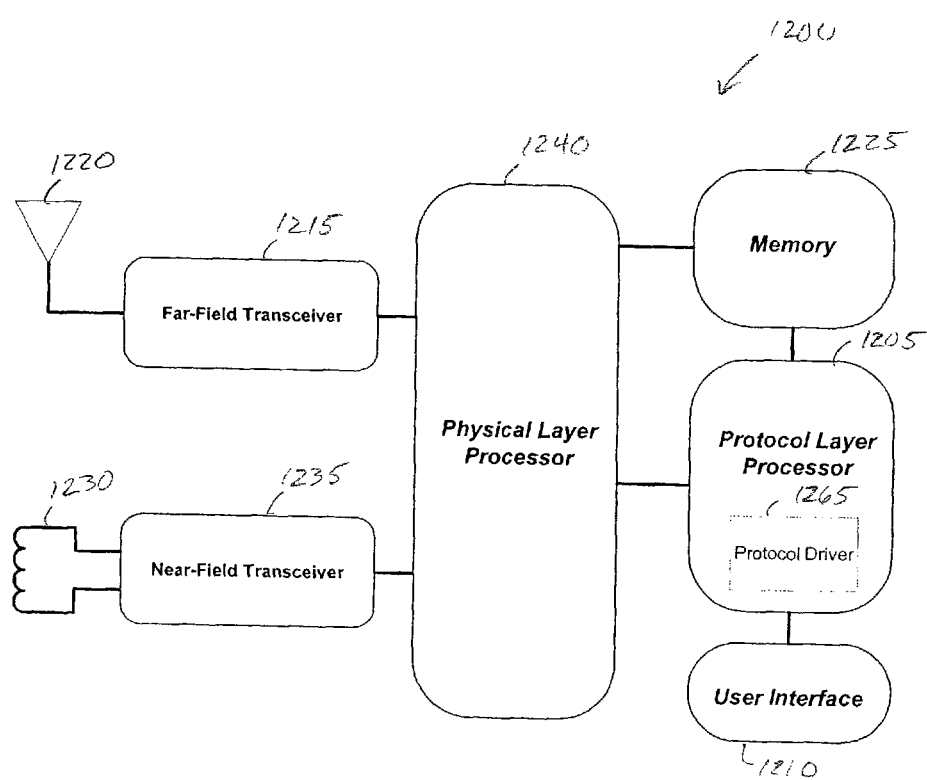
FIG. 12 shows a block diagram of portions of another example of an external telemetry device that includes both a far-field reconfigurable RF telemetry system and a near-field telemetry system.

According to some examples, the external telemetry device 500 is adapted to optionally communicate with an IMD using near-field telemetry. FIG. 12 shows a block diagram of portions of an example of an external telemetry device 1200 having a physical layer and a protocol layer. The protocol layer includes a protocol layer processor 1205, a protocol layer memory 1225 and a user interface 1210. The protocol layer also includes a plurality of protocol drivers 1265. The protocol drivers 1265 can be stored in the protocol layer memory 1225 or in a second memory, such as a memory included in the protocol layer processor 1205. The protocol drivers 1265 include a plurality of protocol drivers corresponding to a plurality of IMD types that communicate using near-field telemetry.

The physical layer includes a configurable near-field transceiver circuit 1235, a near field antenna 1230, a far field transceiver circuit 1215, a far-field antenna 1220, and a physical layer processor 1240 in electrical communication with the protocol layer processor 1205. In some examples, a single processor performs the functions of the protocol layer processor 1205 and the physical layer processor 1240. In an illustrative example, the external telemetry device 1200 communicates with an IMD using mutual inductance. In mutual inductance, the near-field antennas of the external telemetry device 1200 and the IMD are placed proximate to one another so that energy generated in a near-field coil antenna 1230 of the external telemetry device 1200 creates energy in a near-field coil antenna of the IMD. Presence of energy at a predetermined time corresponds to a "one" bit and absence of energy at a predetermined time corresponds to a "zero" bit.

A near-field protocol driver defines the content and order of the bytes of data transmitted by the physical layer to an IMD that communicates by near-field telemetry and the content and order of the bytes of data received by the physical layer from the IMD. Upon receiving a signal from the user interface, the protocol layer processor 1205 successively loads the near-field protocol drivers and transmits an IMD interrogation message associated with a loaded protocol driver until a response message is received. If a response message is received, the protocol layer of the external telemetry device 1200 continues to communicate information using the loaded protocol driver associated with the response message.

In some examples, interrogation messages are transmitted until a response message is received that identifies an IMD type. The protocol layer processor 1205 then enables a far-field RF modulation type from the plurality of modulation types according to the identified IMD type. This is useful during a procedure implanting an IMD to first identify the IMD with near-field telemetry and then communicate using far-field telemetry after the identification. This allows the near-field telemetry to securely wake-up the IMD, but the far-field telemetry allows communication while the device is in a sterile field without requiring a near-field telemetry wand to enter the sterile field.

Figure 13:
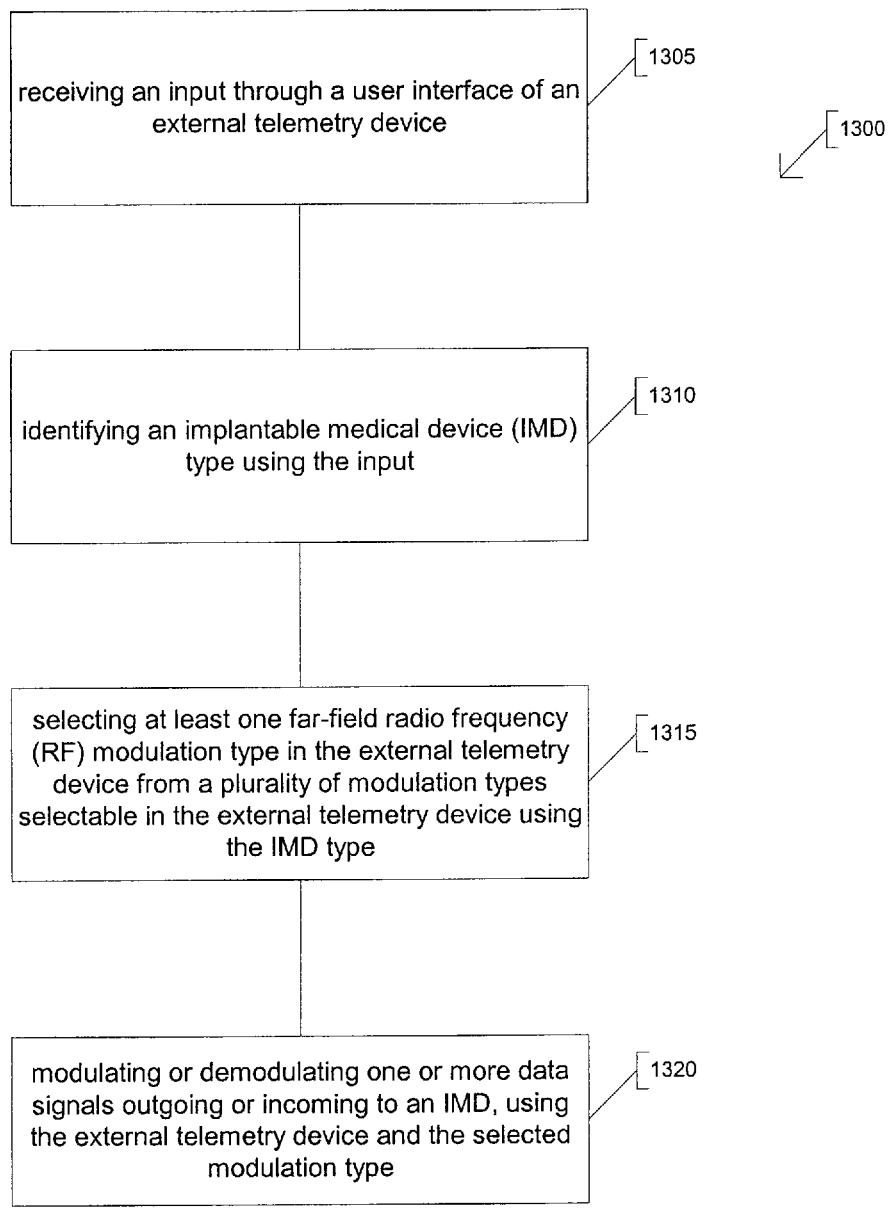
FIG. 13 is a block diagram of a method of providing bi-directional communication with IMDs.

FIG. 13 is a block diagram of a method 1300 of providing bi-directional communication with IMDs. At 1305, an input is received through a user interface of an external telemetry device. At 1310, an implantable medical device (IMD) type is identified using the input. In some examples, the identifier is entered using a keyboard, mouse, or touch screen, and the user is provided visual feedback through a display. In some examples, the identifier includes an IMD model number, or an IMD serial number, or the like. In some examples, the identifier is an IMD product name or IMD product family name.

At 1315, a radio frequency (RF) modulation type is selected in the IMD programmer from a plurality of modulation types selectable in the external telemetry device according to the IMD type entered through the user interface. The modulation type is selectable from any of ASK, OOK, FSK, BFSK, GFSK, QFSK, MSK, PSK, BPSK, QPSK, QAM, OFDM, FHSS, and DSSS modulation techniques. At 1320, one or more data signals outgoing or incoming to the IMD are demodulated using the enabled modulation type of the external telemetry device. In some examples, the modulation type or types are selected using the IMD type and using geographic location information loaded into the external telemetry device. In some examples, the modulation type used to modulate outgoing data signals is different from the modulation type used to demodulate incoming data signals.

In some examples, the method 1300 includes first communicating with the IMD using near-field telemetry before using far-field RF modulation. The near-field telemetry may include a wand antenna for mutual inductive telemetry. Initial communication between the external telemetry device and the wand may be done before the IMD is placed in a sterile field during an implant procedure. If the near-field communication is successful and valid, subsequent communication in the sterile field is done using far-field RF modulation. This provides an additional layer of security in communications with an IMD.

According to some examples, the method 1300 includes selecting a communication frequency allocation band and a carrier frequency in the external telemetry device from a plurality of communication frequency allocation bands selectable in the external telemetry device using the IMD type. The communication frequency allocation band is selectable from among the medical implant communication service (MICS) band of 402-405 MHz, the industrial, scientific, and medical (ISM) band of 902-928 MHz, the European short range device (SRD) bands 862-870 MHz, the EU SRD band of 434 MHz, and the Japanese SRD band of 420 MHz-450 MHz. In some examples, the method 1300 includes selecting different carrier frequencies within the communication frequency allocation bands. In some examples, the outgoing data signals are transmit with a different carrier frequency from the incoming data signals.

In some examples, the method 1300 includes selecting a rate to transmit modulated IMD data and a rate to receive modulated IMD data from a plurality of data rates selectable in the external telemetry device according to the IMD type. In some examples, the rate to receive modulated IMD data is different from the rate to transmit modulated IMD data.

In some examples, the method 1300 includes selecting a filter for filtering the outgoing modulated signals and the incoming modulated signals from a plurality of filters selectable in the external telemetry device according to the IMD type. In some examples, selecting a filter includes selecting one of N band filters based upon the communication frequency allocation band selected. In some examples, selecting a filter includes selecting one of N band filters according to the IMD type. In some examples, selecting a filter includes selecting one of N band filters using the IMD type and geographic location of the external telemetry device.

In some examples, the method 1300 includes selecting a coarse power level to transmit data from a plurality of transmit power levels selectable in the external telemetry device using the IMD type. In some examples, selecting a power level includes selecting a programmable gain provided by a D/A circuit. In some examples, the method 1200 includes selecting a power level from −30 decibels (dB) to 0 dB in steps less than or equal to 2 dB. In some examples, the method 1300 includes selecting a receive signal sensitivity gain level from a plurality of receive signal sensitivity gain levels selectable in the external telemetry device using the IMD type.

In some examples, the method 1300 includes selecting a wave-shaping function to wave-shape an outgoing modulated carrier signal from a plurality of selectable wave-shaping functions according to the IMD type. In some examples, selecting a wave-shaping function includes low pass filtering to prevent inter-symbol interference and narrow the transmit signal bandwidth. In some examples, selecting a wave-shaping function includes implementing a low pass FIR filter with a digital signal processor (DSP).

In some examples, the method 1300 includes selecting an IMD communication protocol in the external telemetry device from a plurality of IMD communication protocols selectable in the external telemetry device using the IMD type. A communication protocol defines the content and order of the bytes of data communicated between a type of IMD and an external telemetry device. Typically, the order is determined by a manufacturer's proprietary protocol for an IMD.

In some examples, the method 1300 includes enabling an external device modulation type and communication protocol in the external telemetry device for wireless communication with a second external device. As an illustrative example, the method 1300 includes enabling a modulation type and communication protocol that is included in the IEEE standard 802.11 protocol family. In another example, the method 1300 includes enabling the external telemetry device to communicate using the Bluetooth™ protocol. In another example, the method 1300 includes enabling the external telemetry device to communicate using the ZigBee protocol. IMD data signals outgoing to the second external device are modulated and data signals incoming from the second external device are demodulated using the external device modulation type and communication protocol of the external telemetry device.

In some examples, the method 1300 includes detecting a failure in a modulated signal transmission from a first antenna of the external telemetry device and transmitting outgoing modulated signals and receiving incoming signals using a second antenna in response to one or more detected signal transmission failures. In some examples, detecting a signal transmission failure includes detecting a null resulting from destructive interference from incident and reflected waves of RF signals.

Figure 14:
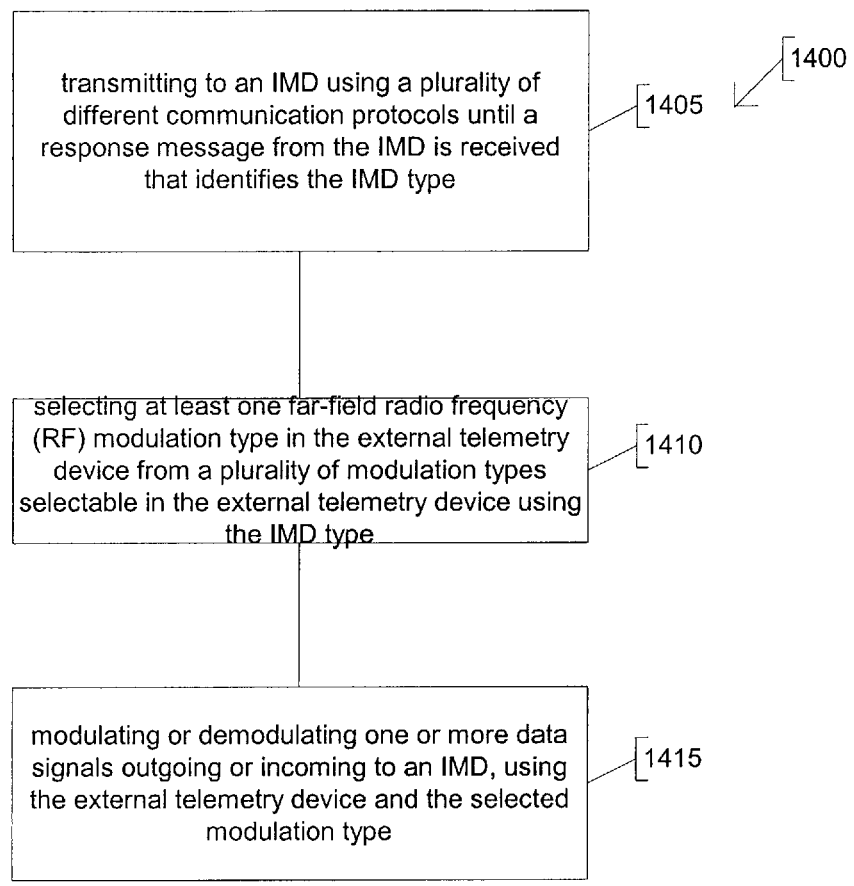
FIG. 14 is a block diagram of another method of providing bi-directional communication with IMDs.

FIG. 14 is a block diagram of another method 1400 of providing bi-directional communication with IMDs. At 1405, a plurality of messages using different communication protocols are transmitted to an IMD until a response message is received that identifies an IMD type. At 1410, a radio frequency (RF) modulation type is selected in the IMD programmer from a plurality of modulation types selectable in the IMD programmer using the IMD type. At 1415, data signals outgoing to an IMD are modulated and data signals incoming from the IMD are demodulated using the enabled modulation type of the identified IMD type. In some examples, the modulation type used to modulate outgoing data signals is different from the modulation type used to demodulate incoming data signals.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system including an external medical data telemetry device to communicate with an implantable medical device (IMD), the external medical data telemetry device comprising:
   a processor;
   a reconfigurable far field radio-frequency (RF) transceiver circuit, operable to modulate an outgoing IMD data signal and to demodulate an incoming IMD data signal using at least one modulation type that is selectable from a plurality of configurable far field RF modulation types by the processor;

at least one far-field antenna, in electrical communication with the reconfigurable RF transceiver circuit, the far field antenna for RF wireless communication with an IMD using the RF modulation technique;

a reconfigurable protocol layer configured to determine, according to a protocol driver, content and order of bytes of data for far field RF communication with the IMD, wherein the protocol driver is one of a plurality of protocol drivers loadable from memory that implement different byte-level protocols; and a user interface, in electrical communication with the processor, wherein the processor selects the far field RF modulation type and protocol driver using information entered by a user.

2. The system of claim 1, wherein the user interface is adapted to communicate to the processor an IMD type entered by a user, and wherein the reconfigurable RF transceiver circuit implements receive demodulation and transmit modulation using the IMD type.

3. The system of claim 2, wherein the reconfigurable RF transceiver circuit includes a local oscillator frequency generation circuit, wherein the local oscillator frequency generation circuit is adapted to generate at least one local oscillator frequency within a communication frequency allocation band, and wherein the communication frequency allocation band is selectable by the processor from a plurality of communication frequency allocation bands using the IMD type.

4. The system of claim 3, wherein the processor is configured to select the communication frequency allocation band using a geographic location.

5. The system of claim 2, wherein the reconfigurable RF transceiver circuit is adapted to modulate data at a data rate selectable from a plurality of data rates using the IMD type.

6. The system of claim 2, comprising a physical layer that includes a programmable filter in communication with the processor, to filter one or more outgoing modulated signals and one or more incoming modulated signals, and wherein the processor is configured to select a filter from a plurality of filters using the IMD type.

7. The system of claim 2, wherein the reconfigurable RF transceiver circuit includes an adjustable transmit power circuit to automatically adjust the transmit power of the reconfigurable RF transceiver circuit using the IMD type.

8. The system of claim 2, wherein the reconfigurable RF transceiver circuit includes an adjustable receive sensitivity circuit to automatically adjust the receive sensitivity level of the reconfigurable RF transceiver circuit.

9. The system of claim 8, wherein the reconfigurable RF transceiver circuit includes:

a receive signal measurement circuit; and an adjustable transmit power circuit, wherein the processor circuit is adapted to automatically adjust the transmit power of the reconfigurable RF transceiver circuit using a measured receive signal strength.

10. The system of claim 2, wherein the reconfigurable RF transceiver circuit includes a programmable wave-shaping circuit to wave-shape an outgoing modulated signal using one of a plurality of wave-shaping functions, and wherein the processor is adapted to select a wave-shaping function for the outgoing modulated carrier signal using the IMD type.

11. The system of claim 1, comprising:

at least a first and a second antennae; and an antenna control circuit, coupled to the reconfigurable RF transceiver circuit and the antennae, the antenna control circuit adapted to detect a signal communication failure from the first antenna and to electrically connect the second antenna to the reconfigurable RF transceiver circuit, in response to one or more signal communication failures.

12. The system of claim 11, wherein the external medical data telemetry device includes a third antenna to communicate data with a second external device.

13. The system of claim 1, comprising:

a physical layer processor to assemble received data into frames and to disassemble frames for transmitting data;

a protocol layer processor;

a first memory in electrical communication with the protocol layer processor and the physical layer processor, to store assembled frames of received data and to store frames of data for transmission by the reconfigurable RF transceiver circuit; and wherein the plurality of protocol drivers are configured for execution on the protocol layer processor, the protocol drivers stored in the first memory or a second memory in electrical communication with the protocol layer processor, wherein the protocol layer processor enables loading of one of the plurality of protocol drivers into a protocol layer processor memory using the IMD type, and wherein the protocol layer processor communicates information with the IMD by storing frames of data in the first memory for transmission to the IMD and reading frames of received IMD data from the first memory using a selected one of the protocol drivers.

14. The system of claim 13, comprising:

a near-field antenna;

a reconfigurable near-field transceiver circuit in electrical communication with the near-field antenna and the protocol layer processor; and wherein the protocol layer processor is adapted, upon receiving a signal from the user interface, to load the protocol drivers and to successively transmit a near field IMD interrogation message associated with various loaded protocol drivers until a response message from an IMD is received that identifies an IMD type, and to enable a far-field RF modulation type from the plurality of modulation types using the identified IMD type.

15. The system of claim 13, wherein the plurality of protocol drivers includes at least one non-proprietary protocol driver for communication with at least one second external device.

16. The system of claim 1, wherein the far field RF transceiver circuit is configurable between a frequency-shift-keying modulation type and a spread spectrum modulation type.

17. The system of claim 1, wherein the far field RF transceiver circuit is configurable between a spread spectrum modulation type and orthogonal frequency division multiplexing (OFDM) modulation.

18. The system of claim 1, wherein the far field RF transceiver circuit is configurable between a phase-shift-keying modulation type and a spread spectrum modulation type.

19. The system of claim 1, wherein the external medical data telemetry device is configured to:

transmit a plurality of interrogation message until a response message is received that identifies an IMD type; and configure the far field RF transceiver circuit using a far field RF modulation type selected from among a plurality of configurable far field RF modulation types according to the identified IMD type.

20. An external medical data telemetry device comprising:
means for receiving an input into the external telemetry device;
means for identifying an implantable medical device (IMD) type using the input;
means for selecting at least one far-field radio frequency (RF) modulation type from a plurality of configurable far field RF modulation types selectable in the external telemetry device using the IMD type;
means for reconfiguring a transceiver in the external telemetry device according to the selected modulation type;
means for loading and configuring a byte-level RF communication protocol from among a plurality of memory stored byte-level RF communication protocols using the IMD type; and
means for modulating or demodulating one or more data signals outgoing or incoming to an IMD, using the external telemetry device and the selectable far field RF modulation type.

* * * * *